(12) United States Patent
Mamourian

(10) Patent No.: US 8,496,603 B2
(45) Date of Patent: Jul. 30, 2013

(54) WIRE TORQUE APPARATUS, WIRE INSERTION DEVICES, IMPROVED ANEURYSM CLIPS AND IMPROVED ANEURYSM CLIP APPLICATORS

(75) Inventor: Alexander Charles Mamourian, Hanover, NH (US)

(73) Assignee: The Trustees of Dartmough College, Hanover, NH (US)

( * ) Notice: Subject to any disclaimer, the term of this patent is extended or adjusted under 35 U.S.C. 154(b) by 375 days.

(21) Appl. No.: 12/512,772

(22) Filed: Jul. 30, 2009

(65) Prior Publication Data
US 2009/0292291 A1 Nov. 26, 2009

Related U.S. Application Data

(62) Division of application No. 11/475,425, filed on Jun. 27, 2006, now abandoned.

(60) Provisional application No. 60/694,271, filed on Jun. 27, 2005.

(51) Int. Cl.
*A61M 25/00* (2006.01)
*A61B 5/00* (2006.01)

(52) U.S. Cl.
USPC .......................................... 600/585; 600/434

(58) Field of Classification Search
USPC ........................................................ 600/585
See application file for complete search history.

(56) References Cited

U.S. PATENT DOCUMENTS

| | | | |
|---|---|---|---|
| 5,104,397 A | | 4/1992 | Vasconcelos et al. |
| 5,137,288 A | * | 8/1992 | Starkey et al. ................. 279/42 |
| 5,161,534 A | * | 11/1992 | Berthiaume ................. 600/434 |
| 5,851,189 A | * | 12/1998 | Forber ........................... 600/585 |
| 5,897,584 A | * | 4/1999 | Herman ........................ 607/122 |
| 6,494,886 B1 | | 12/2002 | Wilk et al. |
| 6,533,772 B1 | * | 3/2003 | Sherts et al. ...................... 606/1 |
| 7,322,995 B2 | | 1/2008 | Buckman et al. |
| 7,717,865 B2 | * | 5/2010 | Boutillette et al. ........... 600/585 |
| 2006/0089670 A1 | | 4/2006 | Hushka |
| 2007/0004991 A1 | * | 1/2007 | Shelton .......................... 600/585 |

OTHER PUBLICATIONS

Solomon, Robert A. and Fukushima, Takanori; "New Aneurysm Clip Appliers for 'Key-Hole' Neurosurgery," Neurosurgery, vol. 28, No. 3, pp. 474-476, 1991.
U.S. Appl. No. 11/475,425, Restriction Requirement mailed Feb. 18, 2009, 9 pages.
U.S. Appl. No. 11/475,425, Response to Restriction Requirement filed Mar. 10, 2009, 9 pages.
U.S. Appl. No. 11/475,425, Office Action mailed May 29, 2009, 8 pages.

* cited by examiner

*Primary Examiner* — Sean P Dougherty
*Assistant Examiner* — Devin Henson
(74) *Attorney, Agent, or Firm* — Lathrop & Gage LLP

(57) ABSTRACT

Wire torque apparatus and methods for engaging a wire torque apparatus are disclosed. Wire insertion devices and methods for inserting a wire into a catheter are disclosed. An improved aneurysm clip utilizes non-metallic material. An improvement to an aneurysm clip applicator tool includes a power supply to power an electromagnet, an adjustable counter element that is attracted to the electromagnet when the electromagnet is magnetized, and a switch to disengage the electromagnet. When the electromagnet is magnetized and comes within a certain proximity to the counter element, the electromagnet and the counter element attract and cling to one another. They are released by activating a switch.

7 Claims, 24 Drawing Sheets

WIRE TORQUE APPARATUS, WIRE INSERTION DEVICES, IMPROVED ANEURYSM CLIPS AND IMPROVED ANEURYSM CLIP APPLICATORS

RELATED APPLICATION

This application is a divisional of U.S. patent application Ser. No. 11/475,425, filed Jun. 27, 2006, now abandoned which claims priority to U.S. Provisional Application Ser. No. 60/694,271, filed Jun. 27, 2005. The aforementioned applications are hereby incorporated by reference.

BACKGROUND

Angiography procedures often use catheters manipulated with the assistance of wires such as shaped wires, micro wires and glide wires. Such wires allow a practitioner (e.g., a physician, surgeon, or nurse) to guide a catheter within vasculature of a patient being imaged (e.g., to guide the catheter into an appropriate blood vessel). Manipulating such wires may be difficult with gloved hands.

One task that may be difficult to perform is threading a shaped wire into a catheter. This task may be required at the beginning of a procedure, or when a procedure requires removal and re-insertion of the wire. Usually an insertion tool resembles a short, hollow cylinder: a wire is loaded into the cylinder and pushed through it into the catheter. In some cases, loading the wire involves pushing a proximal (e.g., patient) end of the wire into the cylinder. However, some wires have a curved proximal end that does not easily insert into the cylinder; in these cases, a distal end of the wire is threaded into a proximal end of the cylinder, and the device is manipulated along the full length of the wire to insert the curved end of the wire into an open end of the catheter. Once insertion is complete, the device is manipulated along the full length of the wire and removed. Guide wires may be over 100 cm in length, so threading the insertion device on, off and along the wire may consume enough time that this time has to be factored into a practitioner's decision to remove and re-engage the wire during a procedure. Re-insertion also provides an unwanted opportunity to drop or contaminate the wire. Also, threading a full length of the wire increases risk of damaging or stripping special coatings (e.g., coatings that allow them to move smoothly within the catheter) of certain wires.

Once a wire is installed in a catheter, the practitioner may need to push, pull and/or twist the wire to direct the wire and the catheter within the subject. Existing torque devices may be helpful in directing the wire, but as with the insertion tool, the torque device must be threaded onto the distal (straight) end of the wire, which may also be time consuming.

FIG. 1A shows a perspective view of one prior art device 10 for manipulating a wire (not shown). Device 10 is made of plastic and has a cap 20 and a handle element 30, as shown. Handle element 30 has a handle 40 coupled with a cylindrical element 50 and segmented cylinder elements 60(1)-60(4). Cylindrical element 50 has threads 55. Handle element 30 forms a central hole (see FIG. 1B) about a wire path 5. Cap 20 has a cylindrical portion 70 and a conical portion 72. Cap 20 forms a central hole 74 along wire path 5. Threads 55 engage corresponding threads inside cap 20, such that cap 20 can screw onto handle element 30. Handle 40 and/or cylindrical portion 70 may have gripping features 45, as shown.

FIG. 1B shows an end view of handle element 30, as seen from cap 20. Each of segmented cylinder elements 60(1)-60(4) is separated from two other such elements by a slot 75, as shown. Wire path 5 (not labeled in FIG. 1B) passes through a central hole 15. In use, a practitioner threads a wire through hole 15 and hole 74 and then screws cap 20 onto handle element 30, forcing elements 60(1)-60(4) into conical portion 72 and squeezing elements 60(1)-60(4) together about the wire. This holds the wire in place so that the practitioner can manipulate the wire by manipulating handle 40.

Other devices for manipulating a wire are shown in U.S. Pat. No. 6,533,772 to Sherts et al., which is incorporated herein by reference.

An aneurysm is a localized dilation of a blood vessel caused by disease or weakening of the vessel wall, and may form a "balloon" shape projecting from the vessel. Rupture of a cerebral aneurysm may cause a stroke. Aneurysm clips are sometimes used to close off an aneurysm to prevent its rupture. Diagnosis and post-treatment assessment of aneurysms may utilize angiography.

FIG. 2A shows a top view of one prior art aneurysm clip 80. Clip 80 is made of titanium, for example. Clip 80 has a spring 82 that biases jaws 86(1) and 86(2) into a closed position. A practitioner applying clip 80 uses an aneurysm clip applicator (e.g., as shown in FIG. 3A and FIG. 3B, or FIG. 18A and FIG. 18B) to squeeze clip 80 at points 84, forcing jaws 86(1) and 86(2) apart so that they may be positioned about a base of an aneurysm. The practitioner utilizes the applicator to manipulate clip 80 until the clip is positioned with jaws 86(1) and 86(2) on either side of the aneurysm, whereupon the practitioner releases the applicator from points 84, returning jaws 86(1) and 86(2) to the closed position and freeing the applicator from clip 80. FIG. 2B shows a side view of clip 80; relative to FIG. 2A, clip 80 is rolled towards the viewer so that jaw 86(1) is in front of, and blocks view of, jaw 86(2).

Because aneurysm clip 80 is made of metal, it may introduce unwanted "flare" and other artifacts into computerized tomography ("CT") and CT angiography images made after its installation. Such artifacts may obscure important details in the images (for example, details relating to residual aneurysm) and generally interfere with interpretation of the images. Furthermore, clip 80, if manufactured of certain materials (e.g., cobalt alloy steel) may be moved by a strong magnetic field such as the 3 Tesla field of magnetic resonance ("MR") systems currently being installed in clinical practices. Movement of clip 80 presents a risk of injury or death to a patient.

FIG. 3A and FIG. 3B show a prior art aneurysm clip applicator 1210 in "open" and "closed" positions respectively. Applicator 1210 has handles 1260(1) and 1260(2) that a practitioner compresses to "open" an aneurysm clip 1205. Applicator 1210 also has a flat spring 1275, and latch portions 1220(1) and 1220(2) (attached to handles 1260(1) and 1260(2) respectively). In FIG. 3A, handles 1260(1) and 1260(2) and spring 1275 are not compressed, and applicator 1210 is in an "open" position with jaws 1240(1) and 1240(2) in a position to grab and manipulate clip 1205 (which is in a "closed" position). Pivot points 1230 and 1250 allow movement of applicator 1210 from the "open" position shown in FIG. 3A to the "closed" position shown in FIG. 3B. Latch portions 1220(1) and 1220(2) are disengaged while applicator 1210 is in the "open" position.

In FIG. 3B, handles 1260(1) and 1260(2), and spring 1275 have been compressed by a practitioner, placing jaws 1240(1) and 1240(2) in the "closed" position, and clip 1205 in the "open" position. When jaws 1240(1) and 1240(2) are in the "closed" position, the practitioner may engage latch portions 1220(1) and 1220(2), as shown, to keep them in the "closed" position without the practitioner having to maintain pressure on handles 1260(1) and 1260(2). When clip 1205 is in a final position for clipping an aneurysm, the practitioner must compress handles 1260(1) and 1260(2) in order to disengage latch portion 1220(1) from 1220(2) to close clip 1205. The additional compression motion required by the practitioner to disengage latch portions 1220(1) and 1220(2) may be disadvantageous because it may "jiggle" clip 1205, potentially causing clip 1205 to be misplaced relative to its intended placement. Some practitioners bend off latch portions 1220(1) and/or 1220(2) in order to avoid such a motion. However, when latch portions 1220(1) and/or 1220(2) are bent off, the practitioner must maintain pressure on handles 1260(1) and 1260(2) to keep them in the "closed" position, which may impair the practitioner's ability to maneuver clip 1205 and may again result in misplacement of clip 1205.

SUMMARY

In one embodiment, a wire torque apparatus includes a handle element and a cap. The handle element includes a handle and at least two segmented cylinder elements, and the handle forms a lengthwise slot. The cap can engage the handle element, and forms a conical cavity and a lengthwise slot. The lengthwise slots of the handle and cap are configured to allow a wire to pass through when the slots are aligned, and the segmented cylinder elements are configured to grip the wire within the conical cavity when the cap engages the handle element.

In one embodiment, a wire torque apparatus includes a block forming (a) a first slot, bounded by a first surface and a second surface, that extends lengthwise through the block, and (b) a second slot that extends from one side of the block through the first surface. A cam rotates within the second slot about an axle. The first slot is configured to accommodate a length of wire, and the cam is operable to grip the wire against the second surface.

A method of engaging a wire torque apparatus about a wire includes rotating a cam in a first direction so that a gripping surface of the cam withdraws from a surface of the apparatus. The wire positions into a slot between the gripping surface and the surface of the apparatus. The cam rotates in a direction opposite the first direction so that the gripping surface engages the wire against the surface of the apparatus.

In one embodiment, a wire torque apparatus includes a first block forming (a) a lengthwise slot and (b) a tapered internally threaded cavity; and a second block forming (a) a lengthwise slot and (b) at least two tapered externally threaded elements. The lengthwise slots are configured to allow a wire to pass through when the slots are aligned, and the threaded elements are configured to screw into the cavity to engage the wire.

In one embodiment, an improved wire torque apparatus is of a type that is configured to clamp a length of wire therein, and includes structure of the apparatus forming a lengthwise slot configured to allow the wire to pass through such that the apparatus can clamp onto the wire without threading an end of the wire through the apparatus.

A method of engaging a wire torque apparatus about a wire includes aligning at least two portions of the apparatus such that slots in each portion align. The wire positions into each of the slots. The portions are manipulated so that the apparatus engages the wire.

In one embodiment, a wire insertion device includes a triangular base with side walls, and an insertion sleeve that forms a lengthwise slit. The base and side walls are configured to facilitate positioning of an angiography wire within the insertion sleeve.

A method of inserting a wire into a catheter includes placing a proximal end of the wire between side walls of a wire insertion device. The proximal end is manipulated against the side walls so that the proximal end passes through a slot into an insertion sleeve. The insertion sleeve is inserted into the catheter, and the wire is pushed through the insertion sleeve into the catheter.

In one embodiment, a wire insertion device includes first and second wire threading elements forming a groove therebetween. The first and second elements have an open position configured to receive a wire and a closed position configured to facilitate insertion of the wire into a catheter.

A method of inserting a wire into a catheter includes separating wire threading elements of a wire insertion device. A portion of the wire is placed between the threading elements, which close about the portion of the wire. A tip formed by portions of the threading elements is placed into a catheter. The wire is pushed through the threading elements into the catheter.

In one embodiment, an improved aneurysm clip utilizes non-metallic material.

In one embodiment, an improvement to an aneurysm clip applicator tool includes a power supply to power an electromagnet, an adjustable counter element that is attracted to the electromagnet when the electromagnet is magnetized, and a switch to disengage the electromagnet. When the electromagnet is magnetized and comes within a certain proximity to the counter element, the electromagnet and the counter element attract and cling to one another. They are released by activating a switch.

A method of applying an aneurysm clip includes squeezing handles of an applicator into a closed position with jaws of the applicator squeezing an aneurysm clip into an open position. Activating a switch holds the applicator in the closed position and the clip in the open position. The clip is positioned, and the switch is activated to release the handles so that the jaws of the applicator release the clip.

BRIEF DESCRIPTION OF DRAWINGS

FIG. 16A through FIG. 16E demonstrate the reduced "flare" in angiographic images produced by aneurysm clips of FIG. 14A or FIG. 15A through 15D, as compared to prior art clips.

DETAILED DESCRIPTION OF DRAWINGS

Figure 4A:
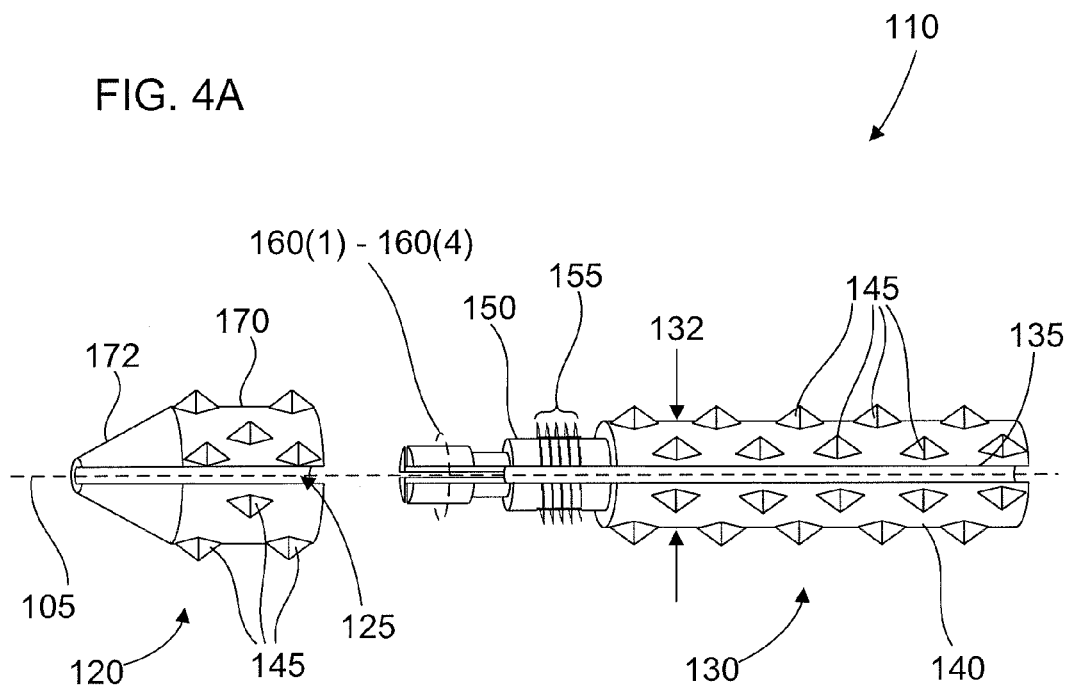
FIG. 4A shows a perspective view of one angiography apparatus 110 for manipulating a wire.

FIG. 4A shows a perspective view of one angiography wire torque apparatus 110, in accord with an embodiment, for manipulating a wire (not shown). FIG. 4A may not be drawn to scale. Device 110 may be made of, for example, plastic, metal, or combinations thereof (e.g., metal parts with plastic coatings). Device 110 includes a cap 120 and a handle element 130, as shown. Handle element 130 has a diameter 132, and has a handle 140 that couples with a cylindrical element 150 and with segmented cylinder elements 160(1)-160(4). Cylindrical element 150 has threads 155. Handle element 130 forms a slot 135 (also see FIG. 4B) about a wire path 105. Cap 120 has a cylindrical portion 170 and a conical portion 172. Inside cylindrical portion 170 (hidden in the view of FIG. 4A) are threads that mate with threads 155 of handle element 30; an inside surface of conical portion 172 forms a conical cavity. Cap 120 forms a slot 125 along wire path 105. Threads 155 engage corresponding threads inside cap 120, such that cap 120 can screw onto handle element 130. Each of handle 140 and cylindrical portion 170 may have gripping features 145, as shown.

Figure 4B:
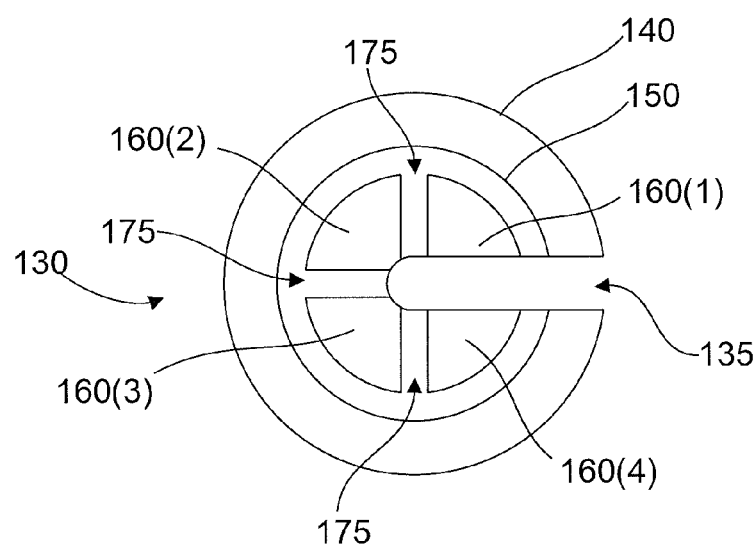
FIG. 4B shows an end view of a handle element of the angiography apparatus of FIG. 4A.

FIG. 4B shows an end view of handle element 130, as seen from cap 120. FIG. 4B may not be drawn to scale. Each of segmented cylinder elements 160(1)-160(4) is separated from two other such elements by slots 135 or 175, as shown. Wire path 105 (not labeled in FIG. 4B) passes through slot 135.

When angiography wire torque apparatus 110 is used, a practitioner positions a wire into wire path 105 through slots 125 and 135, and engages cap 120 onto handle element 130 (by, for example, screwing threads 155 into corresponding threads in cap 120), forcing segmented cylinder elements 160(1)-160(4) into conical portion 180. This squeezes elements 160(1)-160(4) together about the wire, holding the wire in place so that the practitioner can manipulate the wire by manipulating handle 140. Slots 125 and 135 allow positioning of the wire along wire path 105 along any part of the wire that is accessible, so that the wire need not thread through apparatus 110 from an end of the wire. Similarly, wire torque apparatus 110 need not pass over the full length of the wire to disengage from the wire; the practitioner can disengage cap 120 from handle element 130, and pass the wire out of cap 120 and handle element 130 through slots 125 and 135.

It is appreciated that variations on angiography wire torque apparatus 110 are within the scope of this disclosure. For example, a diameter 132 of torque apparatus 110 may vary to suit the preference of a practitioner. Certain practitioners may find that a diameter 132 of less than 5 mm is too small to grasp effectively with gloves, that a diameter 132 of 20 mm or more is unnecessarily large and awkward, and that a diameter 132 of 7 mm to 9 mm is large enough to grip securely yet small enough to use with precision. Similar issues of practitioner preference may also apply to a type and size of gripping features 145, as discussed below with respect to gripping features of other devices. Although torque apparatus 110 is shown with four segmented cylinder elements 160, a wire torque apparatus may utilize fewer or more of such elements. Although torque apparatus 110 is shown with threads 155 for engaging cap 120 to handle element 130, a wire torque apparatus may utilize other mechanisms, such as protrusions that fit into mating slots, or elements that snap together, for engaging cap 120 to handle element 130.

Figure 5A:
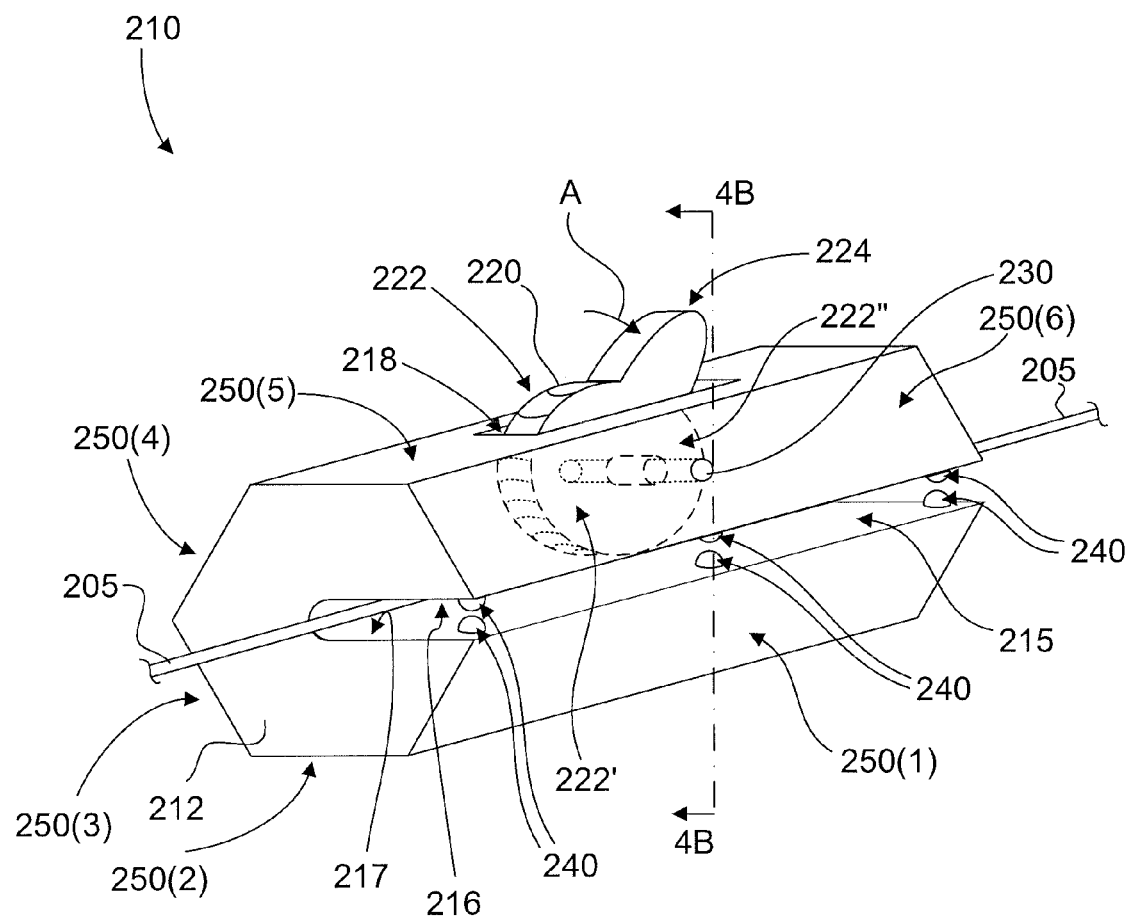
FIG. 5A is a perspective view of one angiography wire torque apparatus, in accord with an embodiment.

FIG. 5A is a perspective view of one angiography wire torque apparatus 210, in accord with an embodiment. FIG. 5A may not be drawn to scale. Apparatus 210 includes a block 212 that forms a slot 215 for an angiography wire 205. Block 212 is hexagonal in cross section, and presents faces 250(1)-250(6) that may be useful for gripping apparatus 210; however, it will be appreciated that block 212 may have a different shape and/or texture for gripping. Block 212 forms buttons 240 at an outer edge of slot 215; buttons 240 are sized such that wire 205 snaps past buttons 240 as it passes into and out of slot 215. A cam 220 with a gripping element 222 and a handle 224 rotates within a slot 218 about an axle 230. Slot 218 extends from top surface 250(5) of block 212 through top surface 216 of slot 215. Axle 230 is shown in FIG. 5A (and FIG. 5B and FIG. 5C) as an element that is separate from cam 220; however axle 230 and cam 220 may be a single structure (e.g., a single piece of molded plastic). Gripping element 222 rotates eccentrically about axle 230. Rotating handle 224 in the direction of arrow A increases clearance between gripping element 222 and a bottom surface 217 of block 212 by moving a large portion 222' of gripping element 222 away from surface 217 and lowering a smaller portion 222" towards surface 217. Rotating handle 224 in the opposite direction of arrow A decreases clearance between gripping element 222 and surface 217 until gripping element 222 contacts surface 217.

Figure 5B:
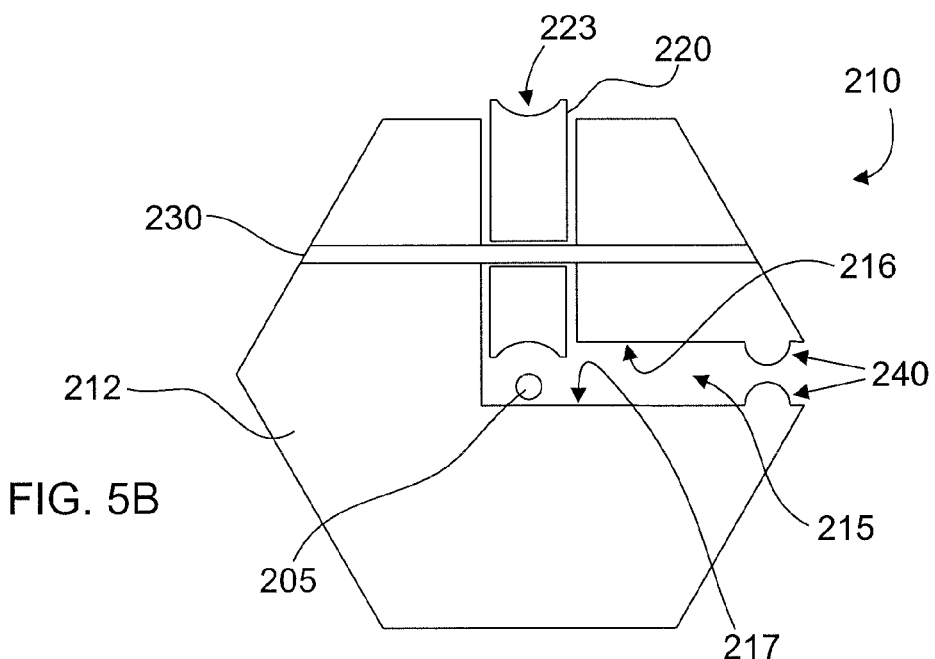
FIG. 5B shows a cross-sectional view of the angiography wire torque apparatus of FIG. 5A, with a cam in an "open" position.

FIG. 5B shows a cross-sectional view of apparatus 210 taken along plane 4B-4B indicated in FIG. 5A, with cam 220 rotated in the direction of arrow A; in this configuration, cam 220 is in an "open" position. FIG. 5B may not be drawn to scale. Angiography wire 205 is shown within slot 215 adjacent to bottom surface 217. Cam 220 has a concave gripping surface 223 that clears wire 25 when cam 220 is in the open position shown in FIG. 5B.

A practitioner uses apparatus 210 as follows. The practitioner first opens cam 220 by rotating it about axle 230 in the direction of arrow A, so that gripping element 222 clears bottom surface 217 of slot 215, as shown in FIG. 5B. The practitioner snaps angiography wire 205 past buttons 240 into slot 215 and rotates cam 220 about axle 230 into a "closed" position, gripping wire 205 between gripping element 222 and surface 217 of block 212.

Figure 5C:
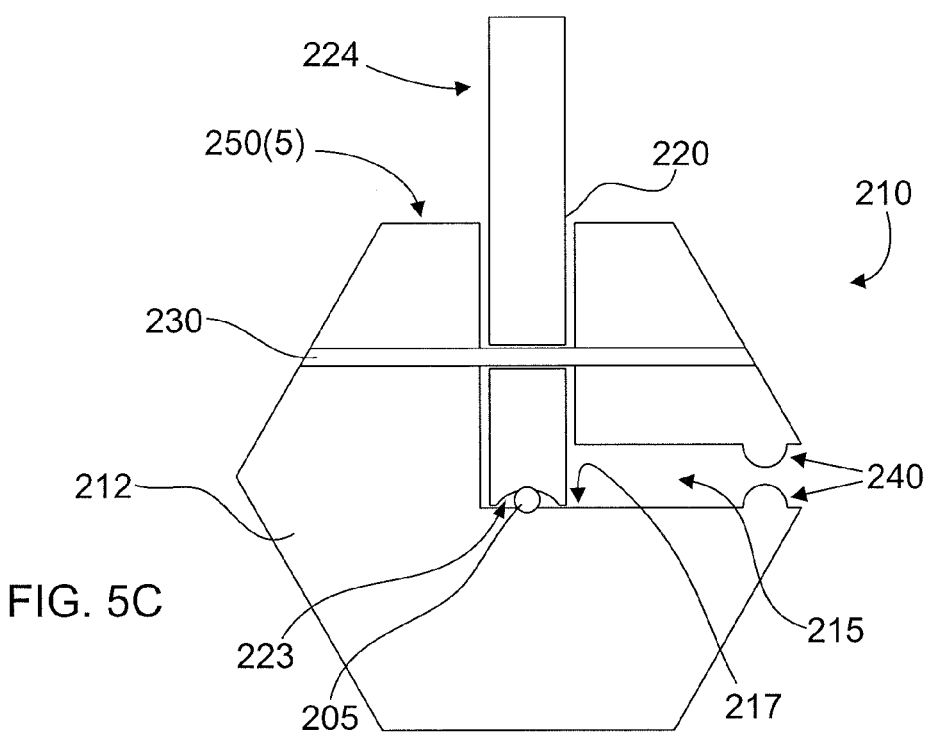
FIG. 5C shows a cross-sectional view of the angiography wire torque apparatus of FIG. 5A, with the cam in a "gripping" position.

FIG. 5C shows a cross-sectional view of apparatus 210 taken along plane 4B-4B indicated in FIG. 5A, with cam 220 rotated in the opposite direction of arrow A, such that cam 220 grips wire 205 against bottom surface 217, forming the closed position. Wire 205 nestles within concave gripping surface 223 and may compress gripping surface 223 and bottom surface 217.

With cam 220 gripping wire 205 against surface 217, the practitioner can manipulate wire 5 by manipulating apparatus 210. Manipulation of apparatus 210 may be easier and more precise than manipulating wire 205 by itself. Furthermore, inserting and removing wire 205 through slot 215 may be easier and faster than threading wire 205 through an end of a torque device, saving the practitioner valuable time during angiography or other catheterization procedures. Buttons 240 provide tactile feedback to the practitioner when inserting wire 205 into slot 215. Buttons 240 may also serve to hold apparatus 210 loosely onto wire 205 when cam 220 is in the open position, so that once wire 205 snaps within buttons 240, the practitioner can use apparatus 210 without concern that apparatus 210 will fall if dropped.

Figure 6A:
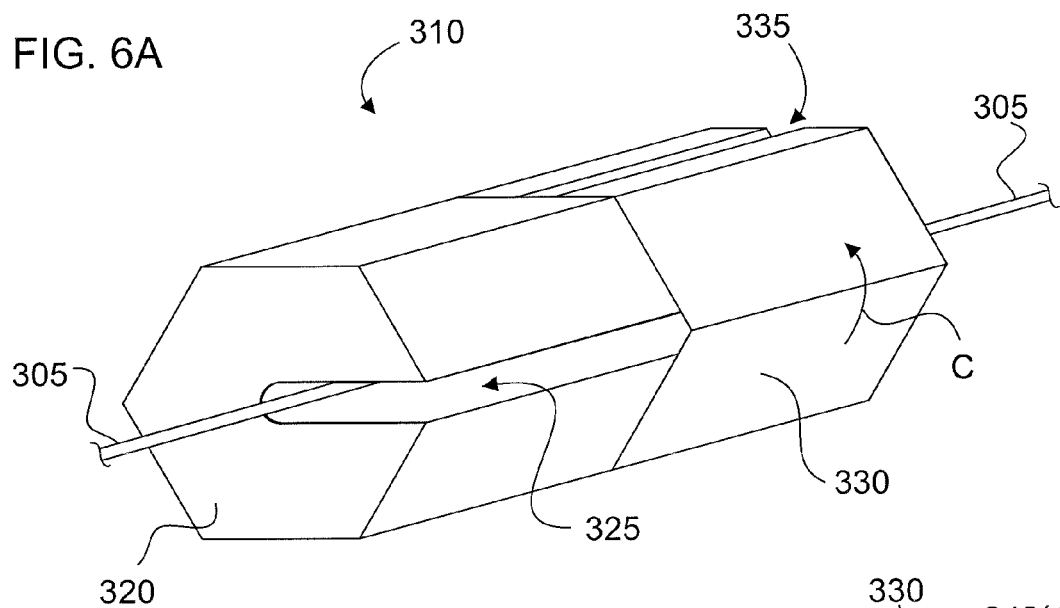
FIG. 6A is a perspective view of one angiography wire torque apparatus, in accord with an embodiment.

FIG. 6A is a perspective view of one angiography wire torque apparatus 310, in accord with an embodiment. FIG. 6A may not be drawn to scale. Apparatus 310 includes two blocks 320 and 330 forming slots 325 and 335, respectively. Apparatus 310 may be made of, for example, plastic, metal, or combinations thereof (e.g., metal parts with plastic coatings). In apparatus 310, blocks 320 and 330 are hexagonal in cross section; it will be appreciated that blocks 320 and 330 may have shapes other than the hexagonal shape shown. FIG. 6A shows blocks 320 and 330 engaged about wire 305 by rotating block 330 in the direction of arrow C relative to block 320, so that apparatus 310 is in a "closed" position, as discussed below.

Figure 6C:
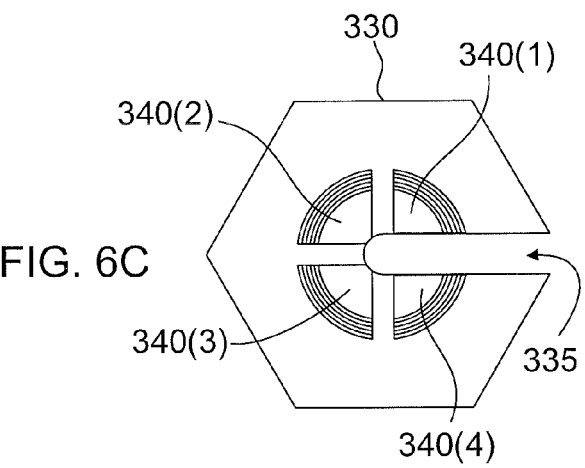
FIG. 6C is an end view of one of the blocks of the angiography wire torque apparatus of FIG. 6A.
Figure 6B:
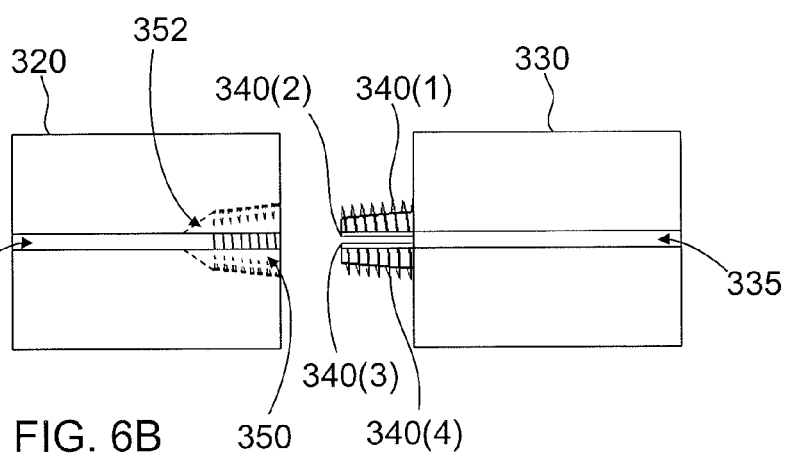
FIG. 6B is a side view of two blocks of the angiography wire torque apparatus of FIG. 6A.

FIG. 6B is a side view of blocks 320 and 330 of apparatus 310 disengaged from each other (i.e., in an "open" position). FIG. 6B may not be drawn to scale. Block 330 includes segmented threaded elements 340(1)-340(4). Threaded elements 340(1)-340(4) (similar to segmented cylindrical elements 160(1)-160(4) of FIG. 4B) are separated by slots; three of the slots extend only through elements 340(1)-340(4); the fourth slot is slot 335, which extends to the other end of block 330, as shown. Block 320 includes a threaded receptacle 350 having a steeply tapered region 352, that intersects slot 325.

FIG. 6C is an end view of block 330 of apparatus 310, as seen from block 320. FIG. 6C may not be drawn to scale. Threaded elements 340(1)-340(4) and slot 335 are shown in FIG. 6C.

When angiography wire torque apparatus 310 is used, a practitioner positions wire 305 into slots 325 and 335, and screws elements 340(1)-340(4) of block 330 into receptacle 350 of block 320 (by rotating block 330 in the direction of arrow C, FIG. 6A). As elements 340(1)-340(4) progress into receptacle 350 and tapered region 352, they squeeze together to hold wire 305 in place (i.e., in the closed position) so that the practitioner can manipulate wire 305 by manipulating apparatus 310. Manipulation of apparatus 310 may be easier and more precise than manipulation of wire 305 by itself. Furthermore, inserting and removing wire 305 through slots 325 and 335 may be easier and faster than threading wire 305 through an end of a torque device, saving the practitioner valuable time during angiography or other catheterization procedures.

Figure 7A:
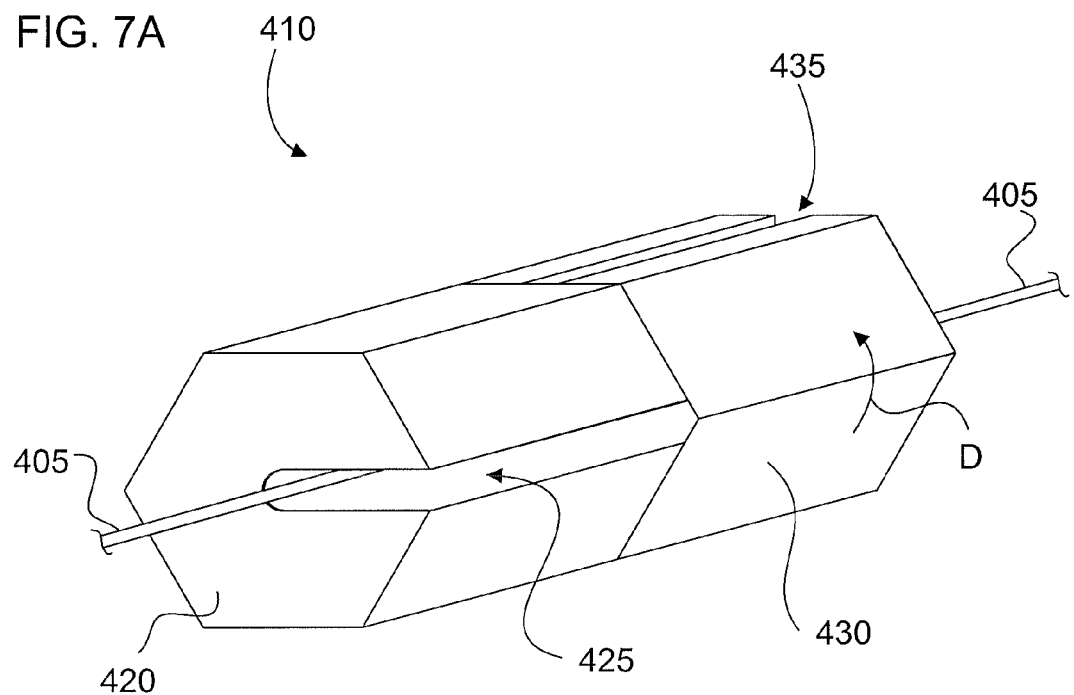
FIG. 7A is a perspective view of one angiography wire torque apparatus, in accord with an embodiment.

FIG. 7A is a perspective view of one angiography wire torque apparatus 410, in accord with an embodiment. FIG. 7A may not be drawn to scale. Apparatus 410 includes two blocks 420 and 430 forming slots 425 and 435, respectively. Apparatus 410 may be made of, for example, plastic, metal, or combinations thereof (e.g., metal parts with plastic coatings). In apparatus 410, blocks 420 and 430 are hexagonal in cross section; it will be appreciated that blocks 420 and 430 may have different shapes. FIG. 7A shows blocks 420 and 430 engaged about wire 405 by rotating block 430 in the direction of arrow D relative to block 420, so that apparatus 410 is in a closed position, as discussed below.

Figure 7B:
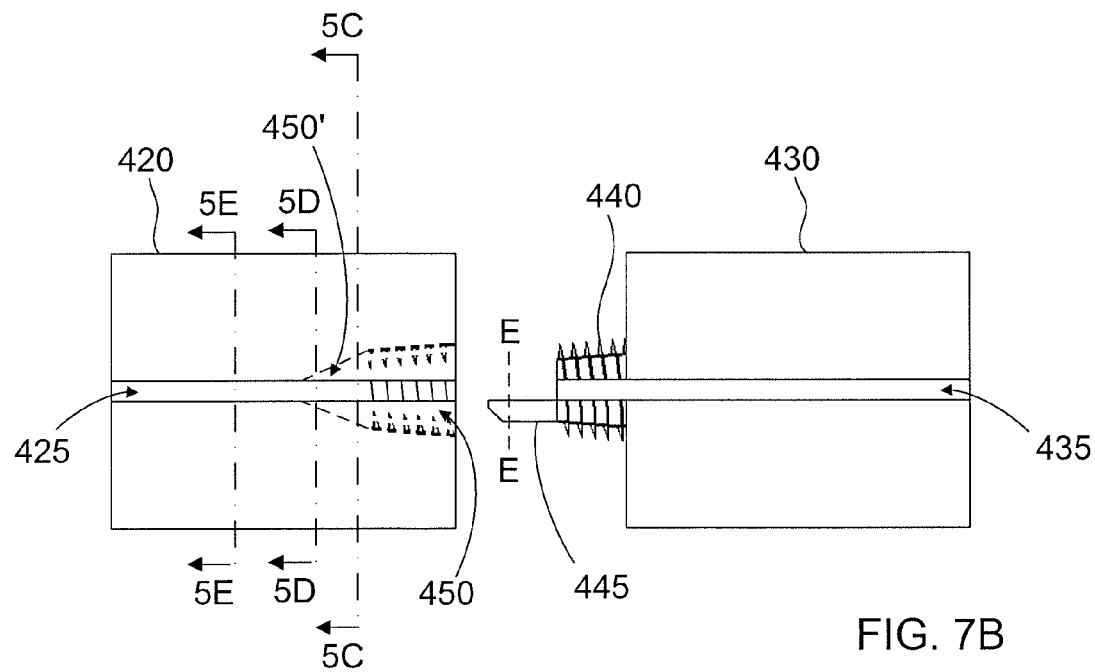
FIG. 7B is a side view of two blocks of the angiography wire torque apparatus of FIG. 7A.

FIG. 7B is a side view of blocks 420 and 430 of apparatus 410 disengaged from each other (i.e., in an open position). FIG. 7B may not be drawn to scale. Block 430 includes a threaded element 440 with a tongue 445; a slot 435 extends through element 440 and to the other end of block 330, as shown. Block 420 includes a partially threaded receptacle 450 that intersects slot 425, as shown.

When angiography wire torque apparatus 410 is used, a practitioner positions wire 405 into slots 425 and 435, and screws element 440 of block 430 into receptacle 450 of block 420 (by rotating block 430 in the direction of arrow D, FIG. 7A). As element 440 advances into receptacle 450, tongue 445 jams wire 405 against block 420 to hold wire 405 in place (i.e., in a closed position) so that the practitioner can manipulate wire 405 by manipulating apparatus 410.

Figure 7C:
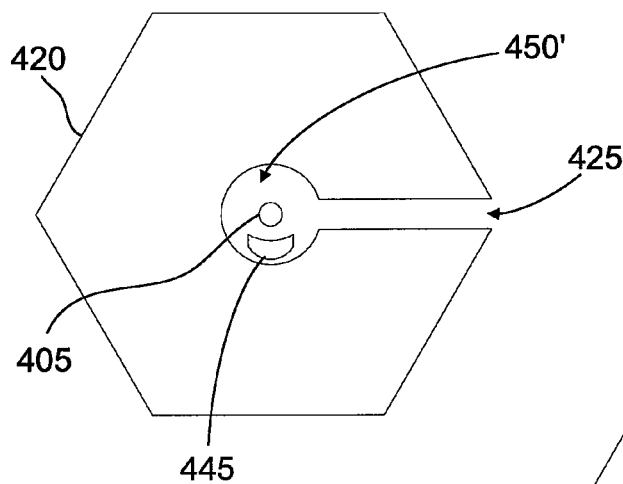
FIG. 7C, FIG. 7D, and FIG. 7E are cross-sectional views of one block of the angiography wire torque apparatus of FIG. 7A.
Figure 7D:
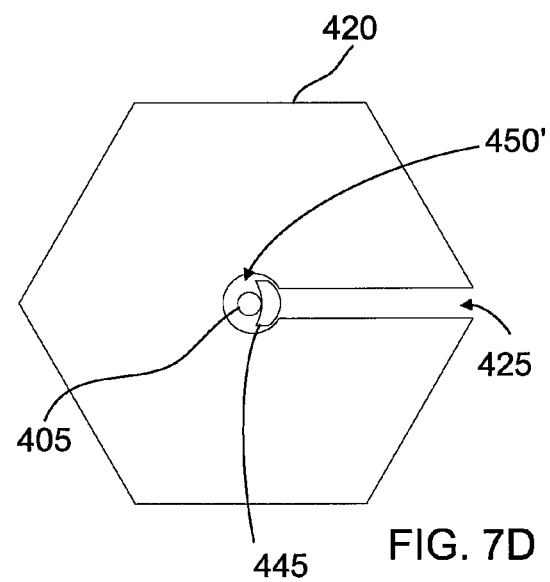
Figure 7E:
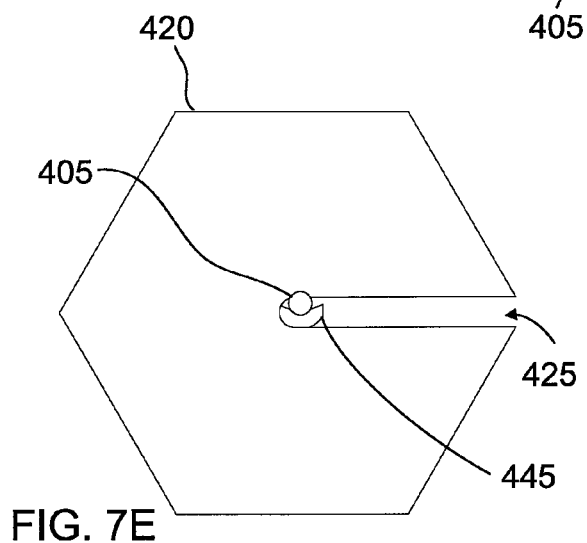

FIG. 7C, FIG. 7D, and FIG. 7E are cross-sectional views of block 420 taken at the planes indicated by dashed lines 6C-6C, 6D-6D and 6E-6E, respectively, in FIG. 7B. FIG. 7C, FIG. 7D, and FIG. 7E may not be drawn to scale. Each of FIG. 7C, FIG. 7D, and FIG. 7E show a cross-section of wire 405 and tongue 445 (at a plane E-E shown in FIG. 7B) as tongue 445 advances into block 420. In FIG. 7C, tongue 445 has just entered a nonthreaded portion 450' of receptacle 450. In FIG. 7D, as element 440 (see FIG. 7B) screws into block 420, tongue 445 advances through nonthreaded portion 450' of receptacle 450; FIG. 7D shows tongue 445 blocking wire 405 from slot 425 (e.g., a closed position). In FIG. 7E, as element 440 screws further into block 420, tongue 445 advances past nonthreaded portion 450' into slot 425 and deforms against block 420 and wire 405.

Manipulation of apparatus 410 may be easier and more precise than manipulating wire 405 by itself. Furthermore, inserting and removing wire 405 through slots 425 and 435 may be easier and faster than threading wire 405 through an end of a torque device, saving the practitioner valuable time during angiography or other catheterization procedures.

Certain modifications of angiography wire torque apparatus 410 are within the scope of the present disclosure. For example, a threaded element like element 440 may be cylindrical instead of cone shaped, and a corresponding threaded receptacle may also be cylindrical. A wire torque apparatus like apparatus 410 may have other numbers of tongues besides the single tongue 445 shown in FIG. 7B, FIG. 7C, FIG. 7D and FIG. 7E; for example, from one to four of such tongues may be utilized.

It is contemplated that other existing types of wire torque apparatus that clamp a wire (such as those illustrated in U.S. Pat. No. 6,533,772 to Sherts et al.) may be improved by forming a lengthwise slot through appropriate elements of such devices, so that the device may clamp at a midpoint of the wire (e.g., without having to manipulate the device from an end of the wire to the location being clamped).

Figure 8A:
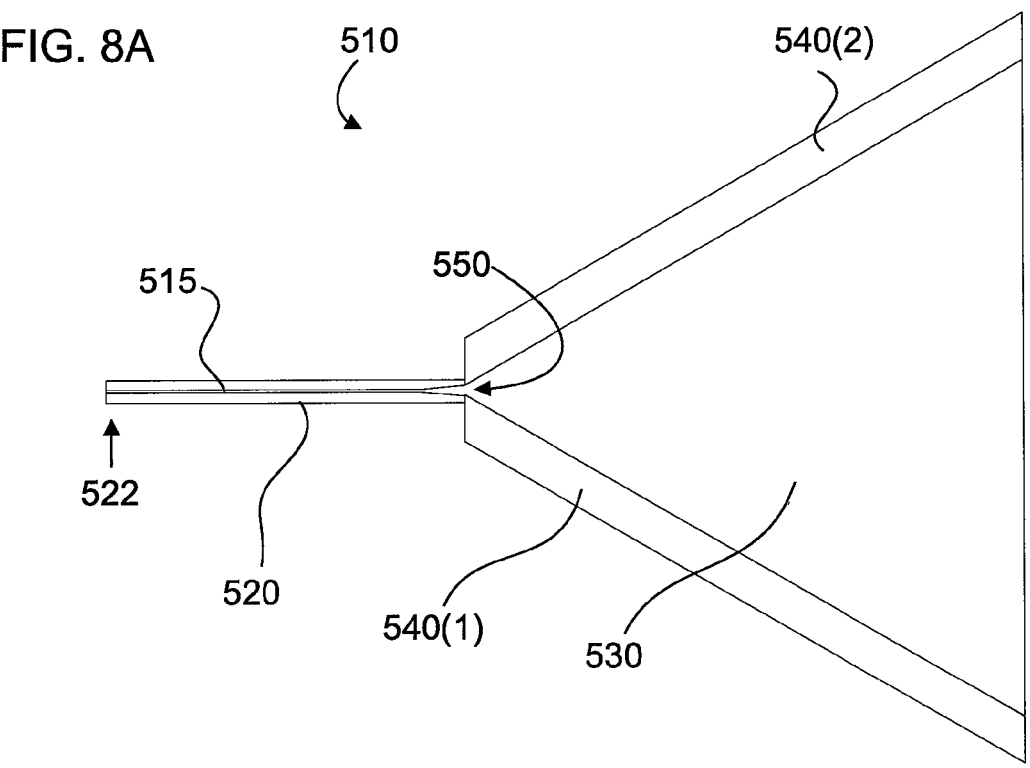
FIG. 8A is a top view of a wire insertion device, in accord with an embodiment.

FIG. 8A is a top view of a wire insertion device 510, in accord with an embodiment. Wire insertion device 510 has a triangular base 530, side walls 540(1) and 540(2), and an insertion sleeve 520, as shown. Side walls 540(1) and 540(2) are separated from each other by a slot 550. Insertion sleeve 520 has a lengthwise slot 515 that meets slot 550 where sleeve 520 meets base 530, as shown. An end 522 of sleeve 550 is sized for insertion into a catheter.

Figure 8B:
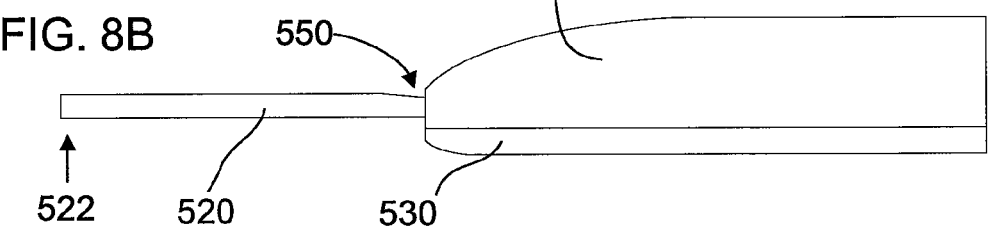
FIG. 8B is a side view of the wire insertion device of FIG. 8A.
Figure 8C:
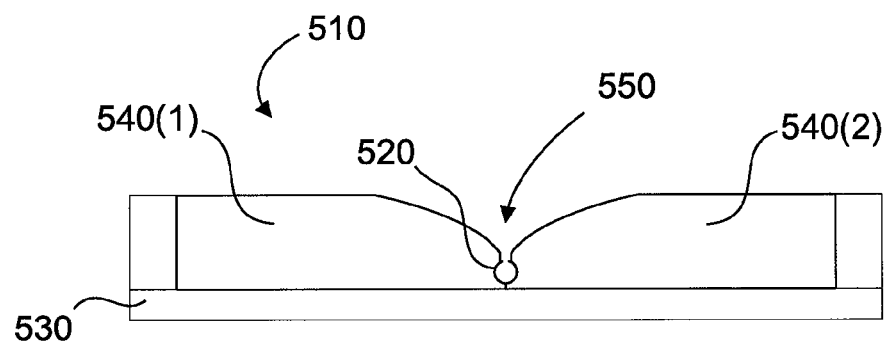
FIG. 8C is an end view of the wire insertion device of FIG. 8A.

FIG. 8B is a side view of wire insertion device 510, showing how sidewalls 540(1) and 540(2) may slope near slot 550. FIG. 8C is an end view of wire insertion device 510, looking from the open side of base 530 toward sleeve 520.

Figure 9A:
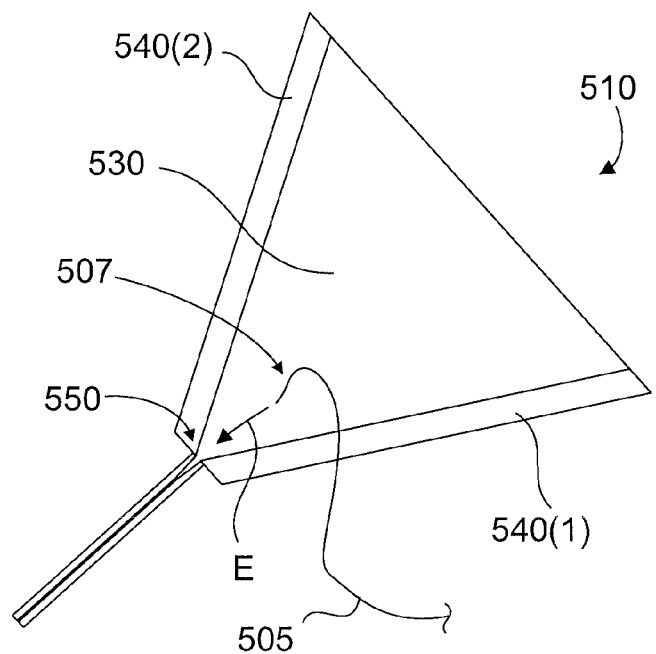
FIG. 9A, FIG. 9B and FIG. 9C illustrate use of the wire insertion device of FIG. 8A with an angiography wire.
Figure 9B:
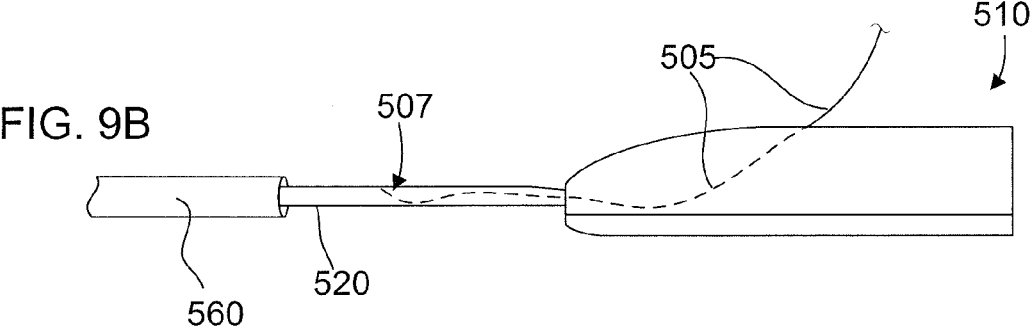
Figure 9C:
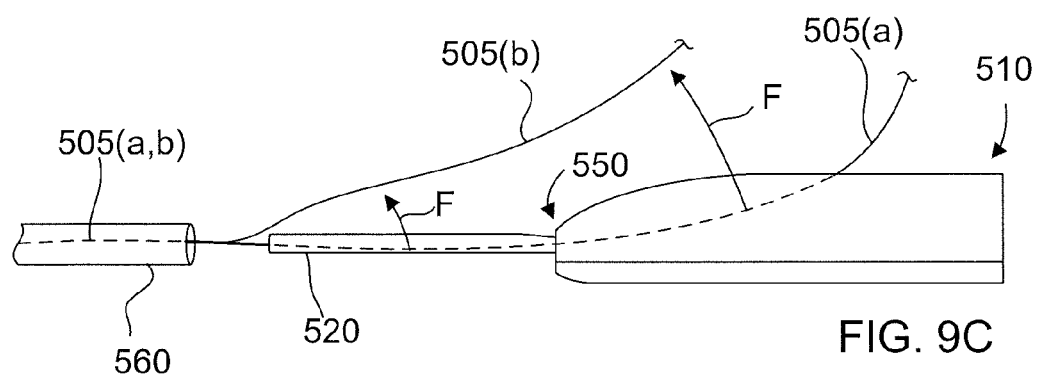

FIG. 9A, FIG. 9B and FIG. 9C illustrate use of wire insertion device 510 with an angiography wire 505. In FIG. 9A, a proximal end 507 (e.g., a patient end) of wire 505 is inserted into sleeve 520 through slot 550 in the direction of arrow E. Base 530 and side walls 540(1)-540(2) provide surfaces which a practitioner may push wire 505 against to urge it into slot 550, which may be especially helpful when proximal end 507 has bends that make wire 505 resist straightening (e.g., to facilitate insertion of wire 505 into sleeve 520). In FIG. 9B, wire 505 has been pushed into sleeve 520, and sleeve 520 has been inserted into a catheter 560. Sleeve 520 is stiff enough, and slit 515 is small enough, that proximal end 507 does not poke out of sleeve 520 through slit 515. FIG. 9C illustrates the removal of wire 505 from wire insertion device 510. Just prior to removal of wire 505, proximal end 507 (not shown) is within catheter 560, wire insertion device 510 is withdrawn from catheter 560, and wire 505 is in the position labeled 505(*a*). A practitioner lifts wire 505 upwards (e.g., in the direction of arrows F) through slot 550 and slit 515 (not visible in this view of device 510) until wire 505 is in the position labeled 505(*b*), so that wire 505 is clear of device 510 yet remains inside catheter 560. Wire insertion device 510 may thus be removed from wire 505 along any section of wire 505. The entire wire 505 need not be threaded through device 510 for removal of the device at a distal end of wire 505.

Figure 10A:
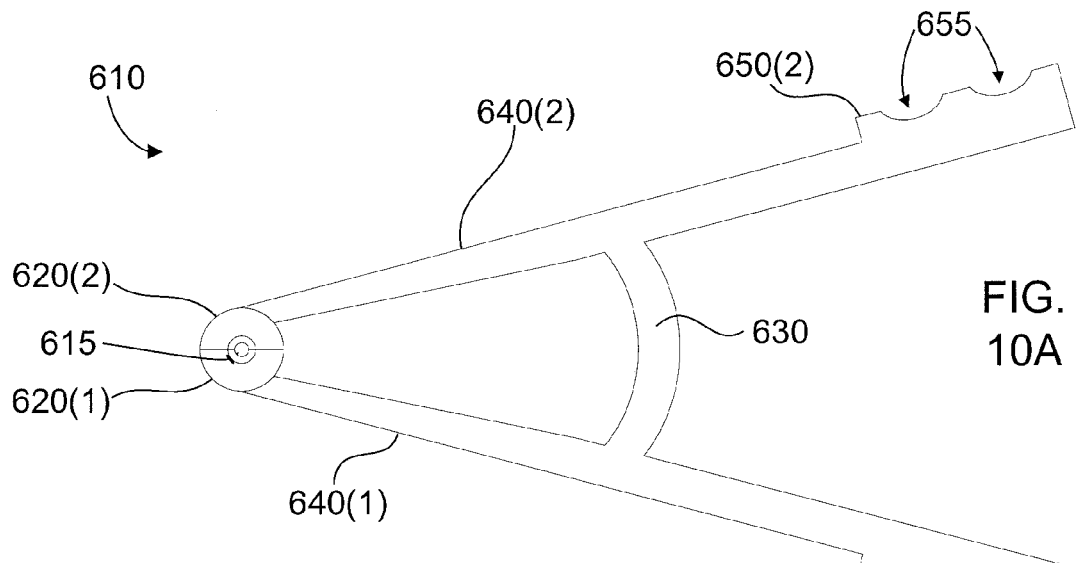
FIG. 10A is a side view of a wire insertion device, in accord with an embodiment.

FIG. 10A is a side view of a wire insertion device 610, in accord with an embodiment. Wire insertion device 610 has two wire threading elements 620(1) and 620(2) that mount on handles 640(1) and 640(2) respectively; between elements 620(1) and 620(2) is a channel 615. Each of handles 640(1) and 640(2) has a grip element, 650(1) and 650(2), respectively, that may include one or more gripping features 655. Gripping features 655 are shown as indentations for fingers; but it will be appreciated that gripping features 655 may also be other shapes, or may be surface textures adapted for gripping (e.g., by a gloved hand). Handles 640(1) and 640(2) couple with a crossbar 630, as shown. Crossbar 630 is a relatively stiff but flexible element that biases handles 640(1) and 640(2) in a closed position (e.g., with wire threading elements 620(1) and 620(2) touching except for channel 615). It will be appreciated that device 610 may be made of plastic, metal, or combinations of plastic and metal (e.g., plastic molded about a metal spring that is within crossbar 630 and handles 640(1) and 640(2)).

Figure 10B:
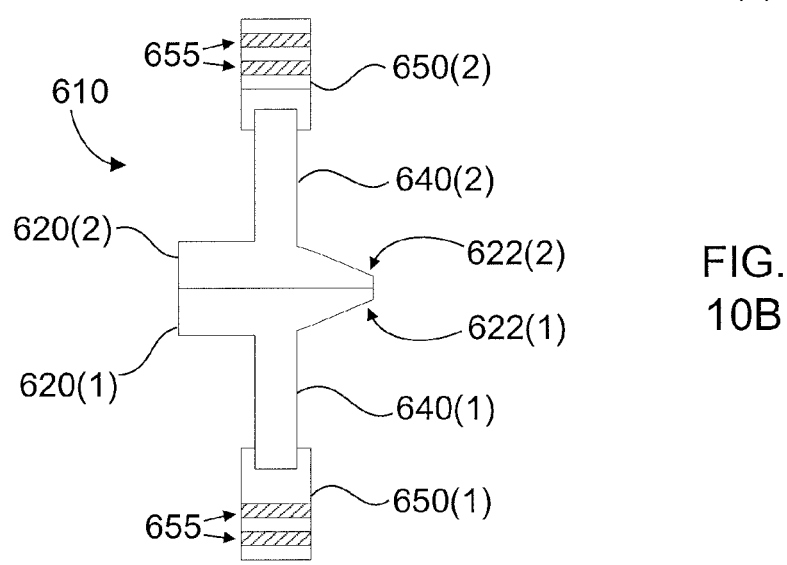
FIG. 10B and FIG. 10C are a front view and a side view, respectively, of the wire insertion device of FIG. 10A.

FIG. 10B is a front view of wire insertion device 610; this view shows wire threading elements 620(1) and 620(2) tapering to tips 622(1) and 622(2), respectively, that are sized for insertion into a catheter. It will be appreciated that a shape and taper of tips 622 may be different from the shape and taper shown in FIG. 10B; for example, tips that taper to a finer point may be used to handle narrower wires.

Figure 10C:
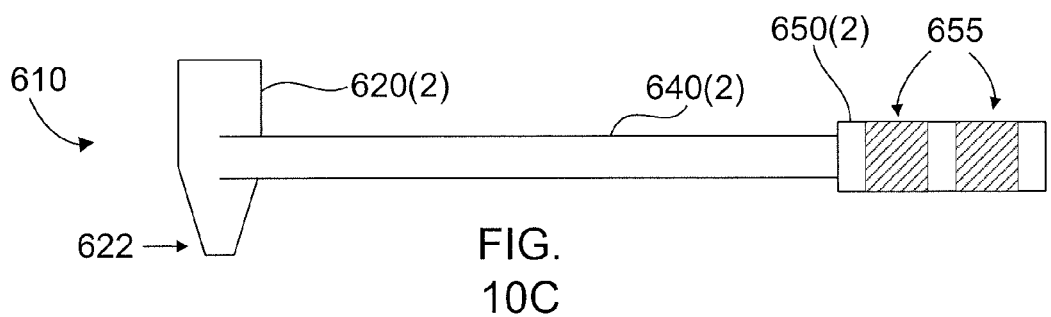

FIG. 10C is a top view of device 610; handle 640(1), crossbar 630 and wire threading element 620(1) are hidden in this view.

Figure 10D:
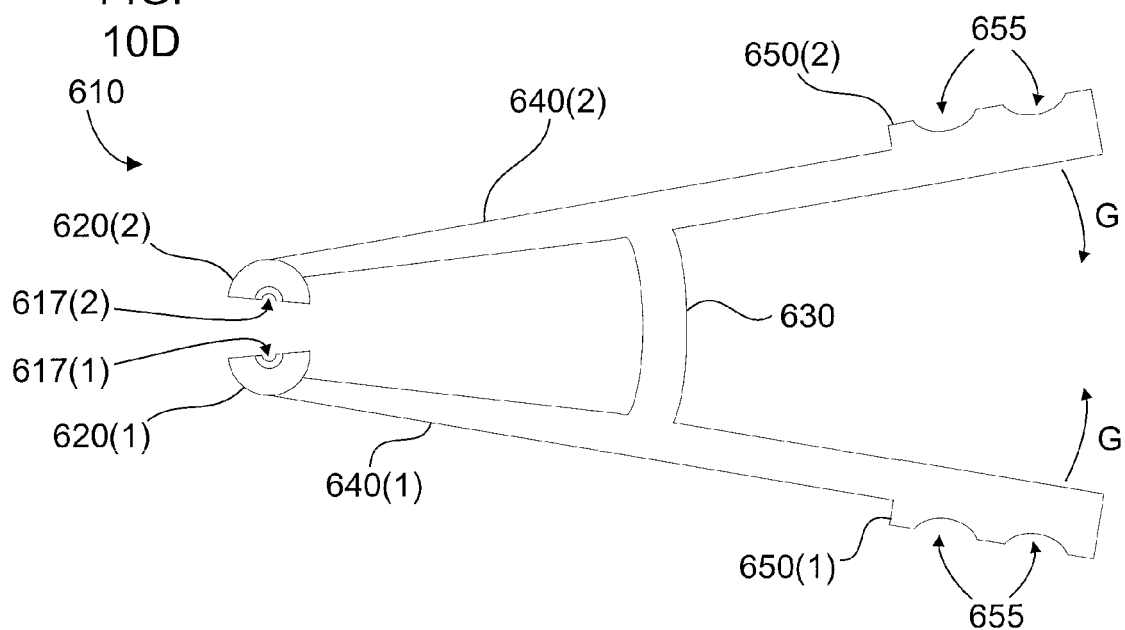
FIG. 10D is a side view of the wire insertion device of FIG. 10A in an open position.
Figure 10E:
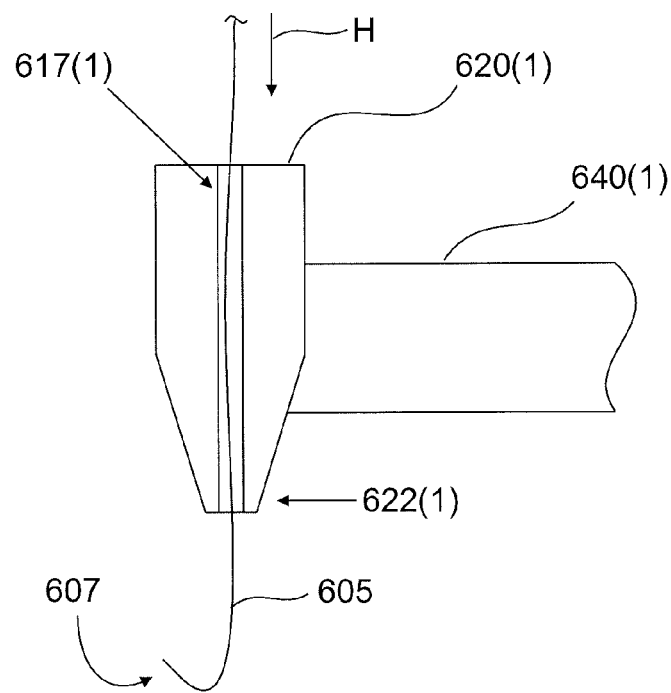
FIG. 10E is an enlarged detail of a wire threading element and a handle of the wire insertion device of FIG. 10A.

FIG. 10D shows device 610 in an open position that forms when handles 640(1) and 640(2) are squeezed together; that is, the handles move in the direction of arrows G. FIG. 10E is an enlarged detail of wire threading element 620(1) and handle 640(1), as seen from above (i.e., as seen from wire threading element 620(2) when device 610 is in the open position), showing a longitudinal groove 617(1) extending through wire grasping element 620(1). An angiography wire 605 is within groove 617(1). Longitudinal groove 617(1) and corresponding longitudinal groove 617(2) in wire threading element 620(2) form channel 615 when device 610 is in the closed position (see FIG. 10A).

To use wire insertion device 610, a practitioner squeezes handles 640(1) and 640(2) together, as shown in FIG. 10D, and places angiography wire 605 within groove 617(1), as shown in FIG. 10E. It will be appreciated that the orientation of device 610 is arbitrary; for example, device 610 may be turned upside down from the position shown in FIG. 10D, and wire 605 may be placed within groove 617(2) instead. The practitioner releases handles 640(1) and 640(2) to close wire 605 in channel 615. The practitioner withdraws wire 605 by pulling it in the direction opposite of arrow H, shown in FIG. 10E, to withdraw a proximal tip 607 of wire 605 into channel 615. If tip 607 is curved, as shown in FIG. 10E, the act of withdrawing tip 607 into channel 615 straightens tip 607 for insertion into a catheter. With device 610 still in the closed position, the practitioner inserts tips 622(1) and 622(2) into a catheter (not shown) and pushes wire 605 in the direction of arrow H to insert wire 605 into the catheter. When a sufficient length of wire 605 is within the catheter, the practitioner withdraws device 610 from the catheter, squeezes handles 640(1) and 640(2) together to open device 610, and removes device 610 from wire 605. Like wire insertion device 510, wire insertion device 610 may thus be used without having to manipulate the device to a distal end of a wire after use.

Figure 11:
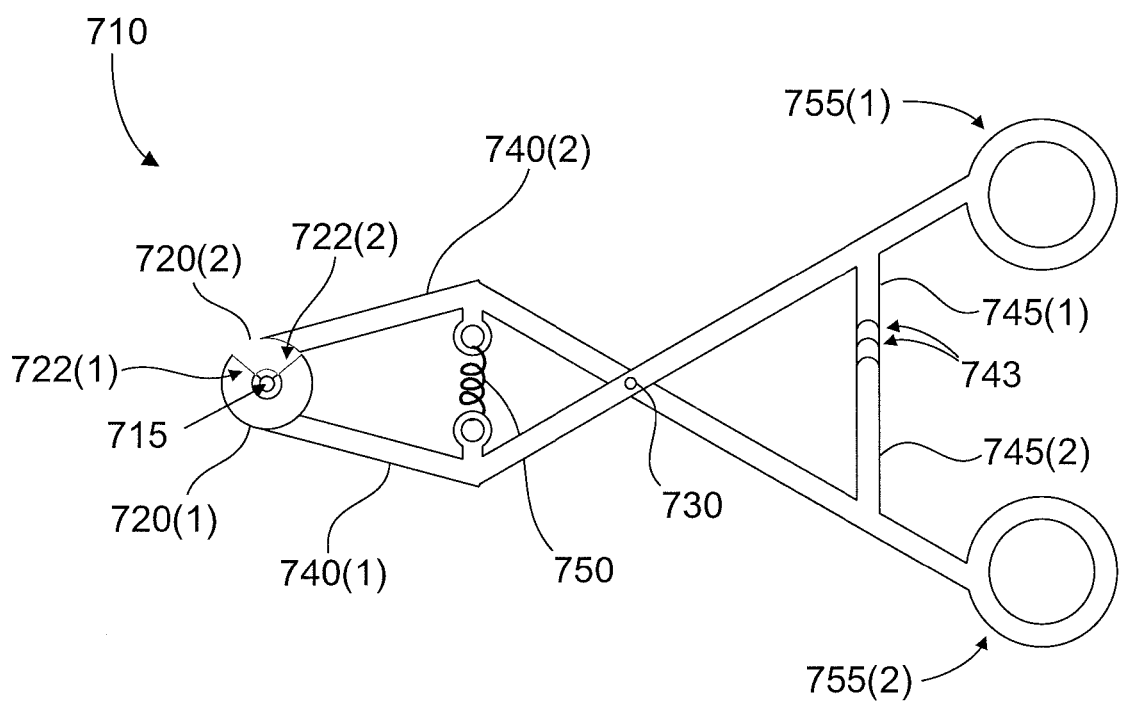
FIG. 11 shows a side view of a wire insertion device, in accord with an embodiment.

FIG. 11 shows a side view of a wire insertion device 710, in accord with an embodiment. Wire insertion device 710 has wire threading elements 720(1) and 720(2) that mount on handles 740(1) and 740(2), respectively; between elements 720(1) and 720(2) is a channel 715. Wire threading elements 720(1) and 720(2) are like wire threading elements 620(1) and 620(2) of wire insertion device 610, except that wire threading element 720(1) has a beveled surface 722(1) that facilitates alignment of a wire within channel 715. Wire threading element 720(2) has a corresponding beveled surface 722(2) such that surfaces 722(1) and 722(2) can close completely about a wire. An axle 730 pivotably joins handles 740(1) and 740(2). Each of handles 740(1) and 740(2) has a gripping feature, 755(1) and 755(2), respectively, that is a loop adapted for use with fingers. Each of handles 740(1) and 740(2) also has a closure element, 745(1) and 745(2), respectively, that have teeth 743 for latching device 710 closed (e.g., elements 745(1) and 745(2) and teeth 743 act like the closure elements of a hemostat). Wire threading elements 720(1) and 720(2) are biased towards each other, into the closed position shown in FIG. 11, by an elastic element 750 (e.g., a spring, but other devices such as elastic or rubber bands may also be used). It will be appreciated that wire insertion device 710 is used much like wire insertion device 610, except that the action of axle 730 requires spreading of the gripping elements to open the device. For example, a practitioner may spread gripping elements 755(1) and 755(2) apart to open device 710. A wire (not shown) is then placed in channel 715 and handles 740(1) and 740(2) are released to close elements 720(1) and 720(2) about the wire, optionally engaging teeth 743. The wire may be partially withdrawn so that a proximal tip of the wire is within channel 715. Tips of elements 720(1) and 720(2) are inserted into a catheter. The wire is inserted into the catheter. The practitioner may withdraw elements 720(1) and 720(2) from the catheter and, alternatively, open device 710 to remove it from the wire, or leave device 710 closed about the wire (e.g., with teeth 743 engaged).

Figure 12A:
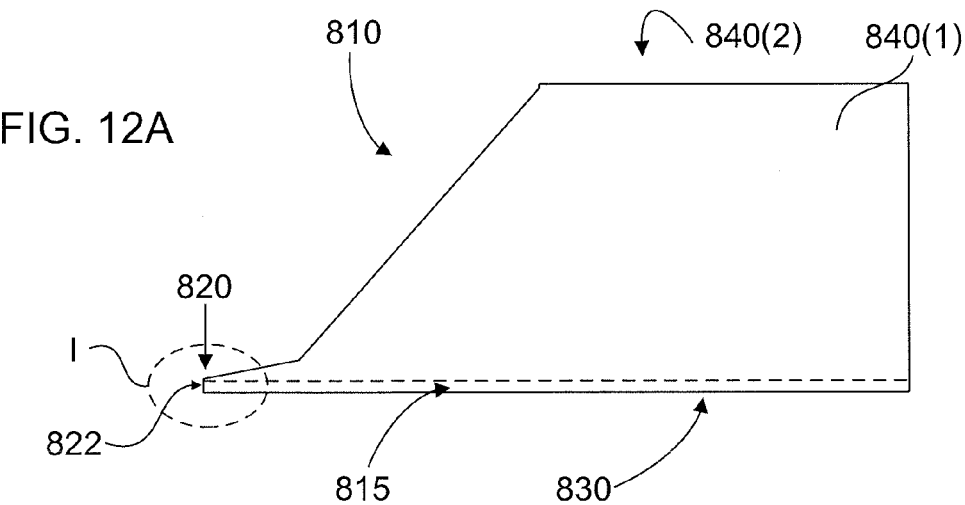
FIG. 12A is a side view of a wire insertion device.
Figure 12B:
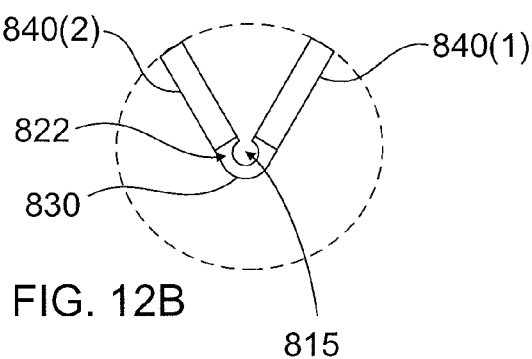
FIG. 12B shows an enlarged end view of a region of the wire insertion device of FIG. 12A.

FIG. 12A is a side view of a wire insertion device 810, in accord with an embodiment. Wire insertion device 810 includes two side elements 840(1) (shown) and 840(2) (hidden behind element 840(1) in this view) that are joined by a hinge element 830 and that form a channel 815, as shown in FIG. 12B. Device 810 forms a tip 820 and a tip surface 822 that are adapted for insertion into a catheter. Device 810 may be made out of metal and/or plastic.

FIG. 12B shows an enlarged end view of a region I of wire insertion device 810. Channel 815 forms where side elements 840(1) and 840(2) connect via hinge element 830. Hinge element 830 may be, for example, a plastic hinge formed concurrently with side elements 840(1) and 840(2) (e.g., device 810 may be molded as one piece). Alternatively, tip surface 822 and hinge element 830 may be made of metal, for example, and side elements 840(1) and 840(2) may be plastic elements molded about portions of the metal.

Figure 12C:
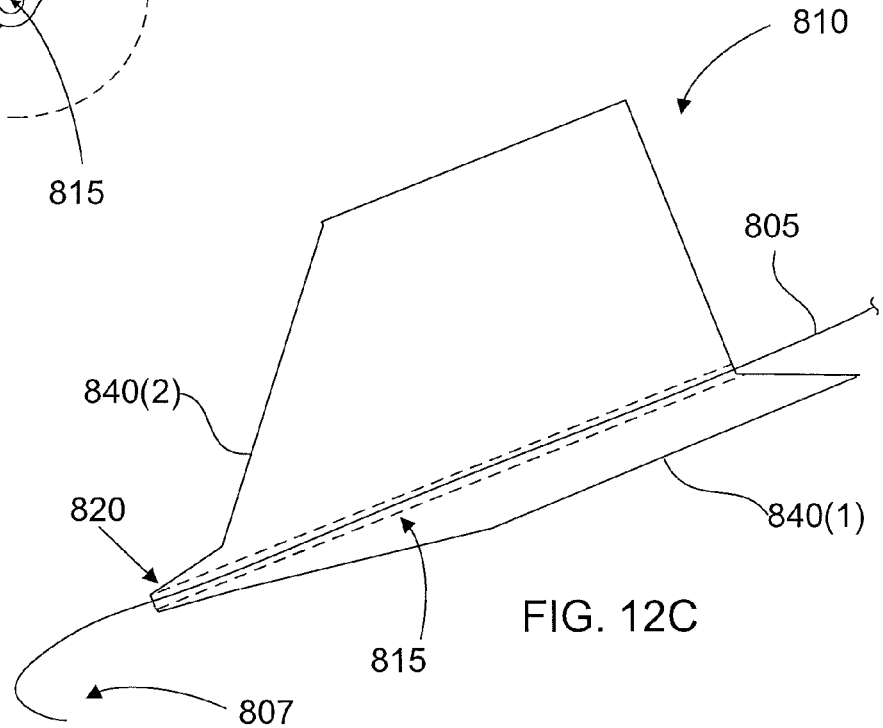
FIG. 12C is a perspective view illustrating the wire insertion device of FIG. 12A during use.

FIG. 12C is a perspective view illustrating device 810 during use. Device 810 is in an open position; that is, side elements 840(1) and 840(2) are positioned away from each other to allow access to channel 815. A practitioner places a midsection of an angiography wire 805 within channel 815, as shown. After wire 805 is within channel 815, the practitioner can (1) close device 810 about wire 805 by pushing side elements 840(1) and 840(2) together, (2) draw wire 805 back through channel 815 so that any curves in proximal tip 807 of wire 805 straighten within channel 815, (3) insert tip 820 of device 810 in a catheter, (4) push wire 805 into the catheter to a sufficient length, (5) withdraw device 810 from the catheter, and (6) release side elements 840(1) and 840(2) so that device 810 can be removed from wire 805.

It will be appreciated that wire insertion devices like device 810 may take various forms. For example, although device 810 is shown with flat side elements 840(1) and 840(2), side elements of other wire insertion devices may be thicker or form different shapes that practitioners may prefer. A closure (e.g., a snap or a latch) may be provided to keep a wire insertion device loosely closed over a wire during procedures wherein a practitioner may anticipate withdrawal and re-insertion of the wire; the closure may be of a type that is easily removed should the practitioner decide that a subsequent re-insertion is not required. Gripping surfaces or features may be provided. Device 810 may include embedded springs, or hinge element 830 may act as a living hinge, to bias the device open. Device 810 may have a relatively long, narrow tip (e.g., region I of FIG. 12A) which may be, for example, a metal cylinder with an opening that adjoins channel 815, suitable for threading a micro wire into a catheter to a sufficient distance that a curved end does not curl up before the walls of the catheter can constrain it from curling up.

Figure 13A:
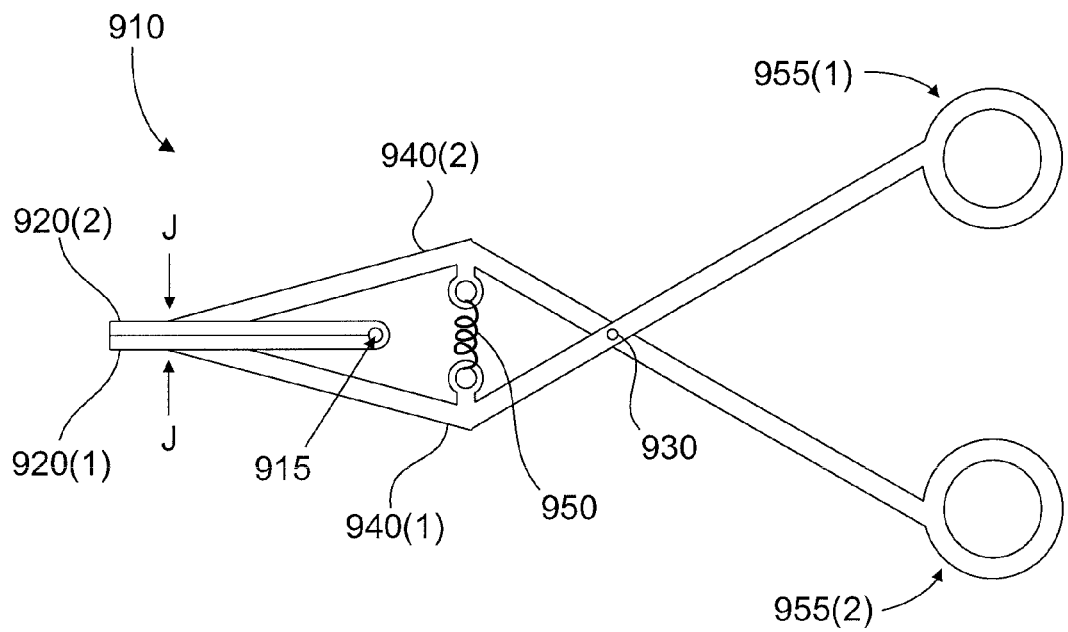
FIG. 13A shows a wire insertion device.

FIG. 13A shows a wire insertion device 910, in accord with an embodiment. Wire insertion device 910 has side elements 920(1) and 920(2) that hingedly couple with handles 940(1) and 940(2), respectively, at points labeled J in FIG. 13A. Between elements 920(1) and 920(2) is a channel 915. An axle 930 pivotably joins handles 940(1) and 940(2). Each of handles 940(1) and 940(2) has a gripping feature, 955(1) and 955(2) respectively, that is a loop adapted for use with fingers. Side elements 920(1) and 920(2) are biased towards each other, into the closed position shown in FIG. 13A, by an elastic element 950 (e.g., a spring, but other devices such as elastic or rubber bands may also be used).

Figure 13B:
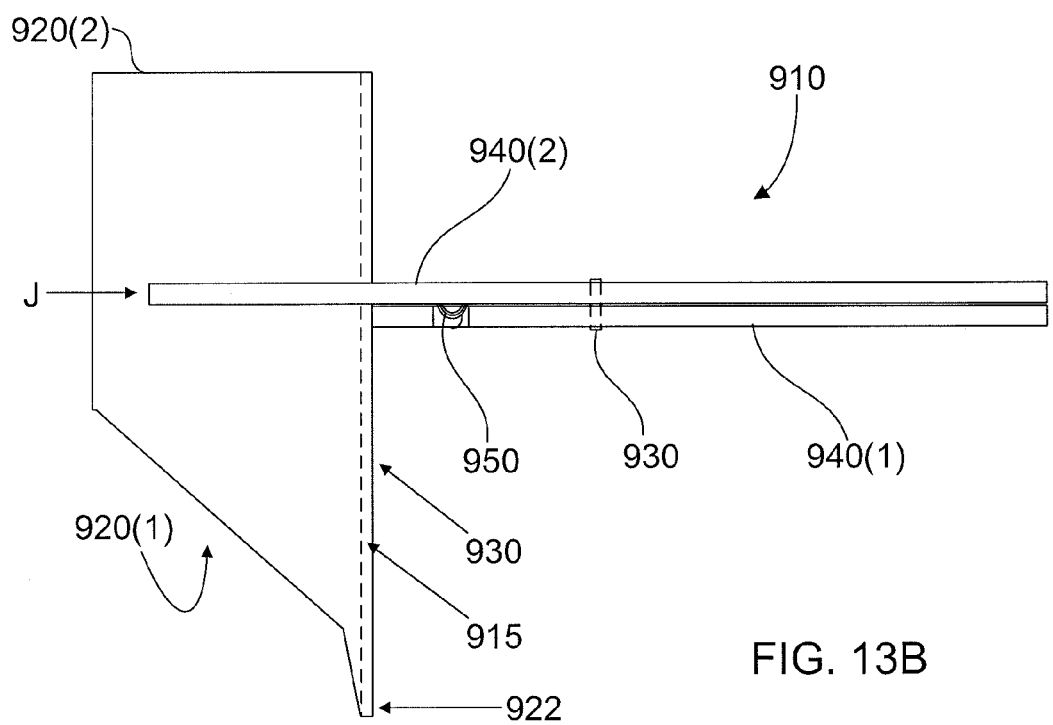
FIG. 13B is a top view of the wire insertion device of FIG. 13A.

FIG. 13B is a top view of wire insertion device 910. Side elements 920(1) and 920(2) are shaped like side elements 820(1) and 820(2) of wire insertion device 810; channel 915 extends between side elements 920(1) and 920(2) inside hinge element 930.

Figure 13C:
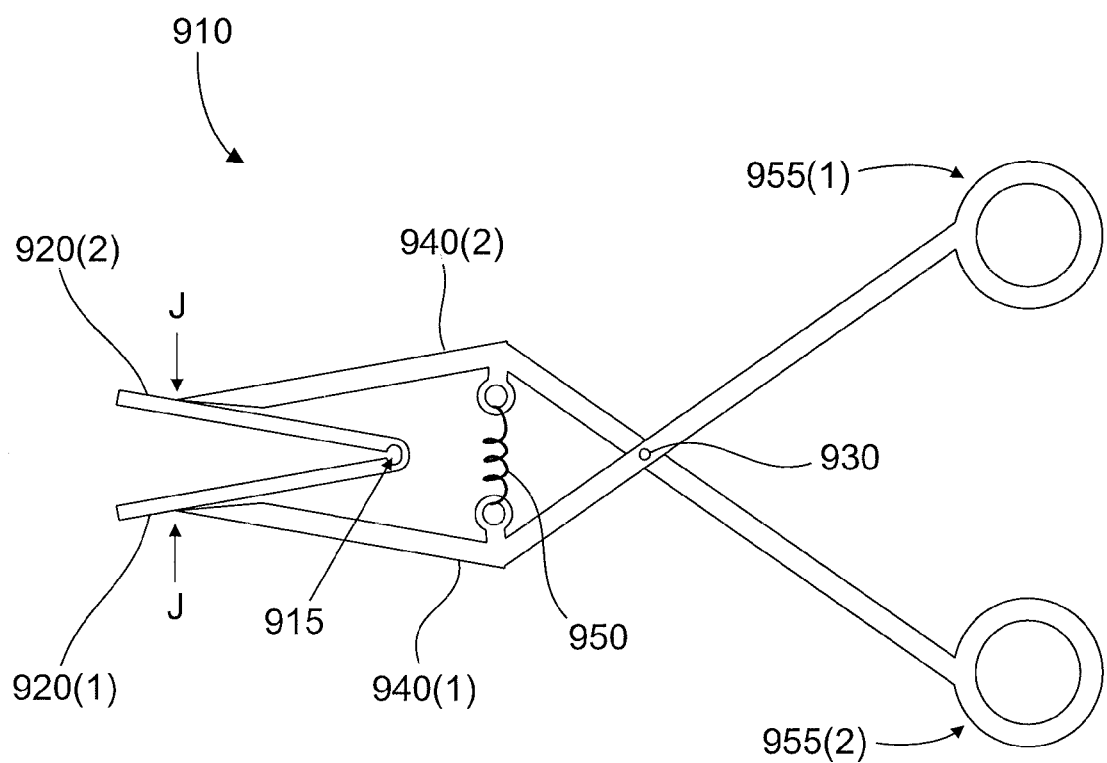
FIG. 13C shows the wire insertion device of FIG. 13A in an open position.

FIG. 13C shows wire insertion device 910 in an open position. The open position forms when gripping elements 955(1) and 955(2) are spread apart from each other, thus spreading handles 940(1) and 940(2), and pulling side elements 920(1) and 920(2) at points J. It will be appreciated that wire insertion device 910 is used much like wire insertion devices 710 and 810. For example, a practitioner may place a midsection of an angiography wire (not shown) within channel 915 and close device 910 about the wire by releasing gripping elements 955(1) and 955(2). The practitioner can draw the wire back through channel 915 so that any curves in a proximal tip of the wire straighten within channel 915. Tip 920 of device 910 is then inserted into a catheter and the wire is pushed into the catheter to a sufficient length. Finally, the practitioner may withdraw device 910 from the catheter and spread gripping elements 955(1) and 955(2) so that device 910 can be removed from the wire.

Figure 1A:
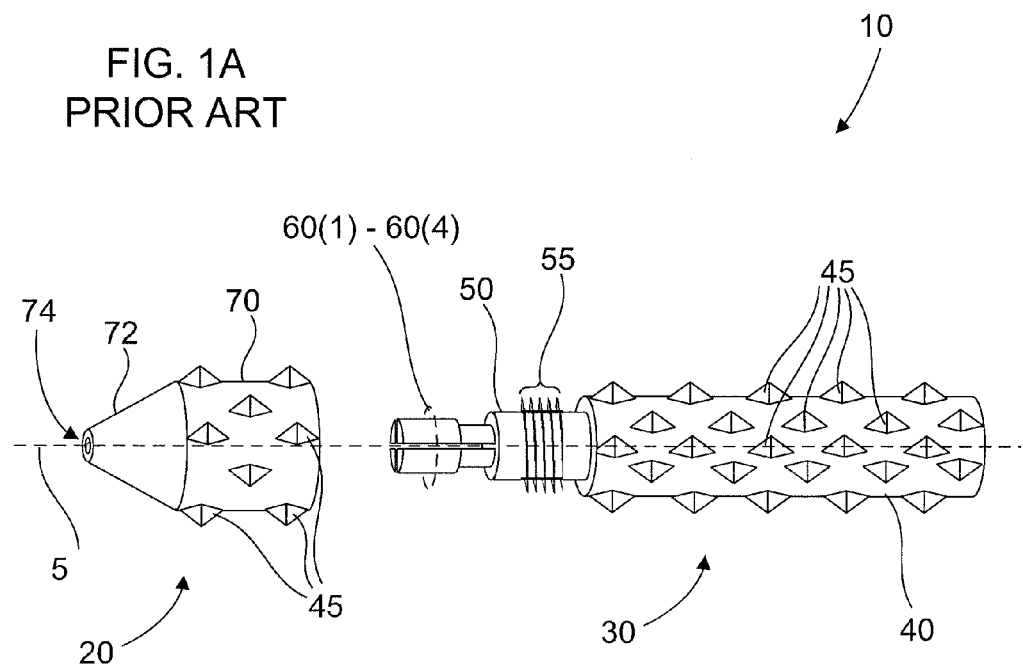
FIG. 1A is a perspective view of a prior art device for manipulating a wire.
Figure 1B:
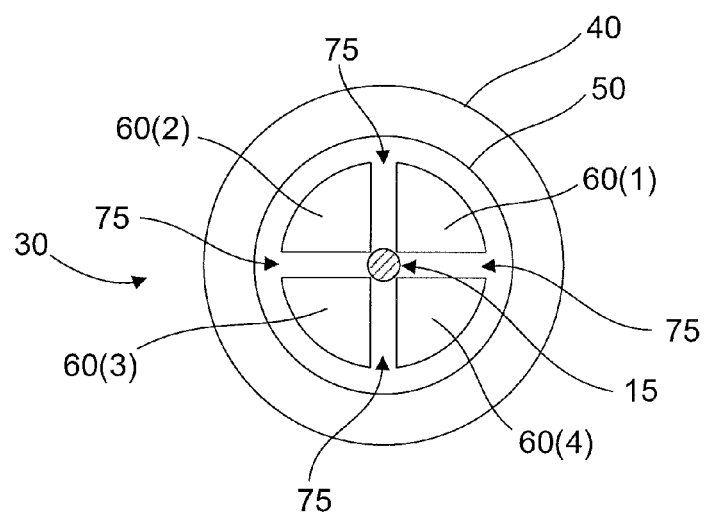
FIG. 1B is an end view of a handle element of the device of FIG. 1A.
Figure 2A:
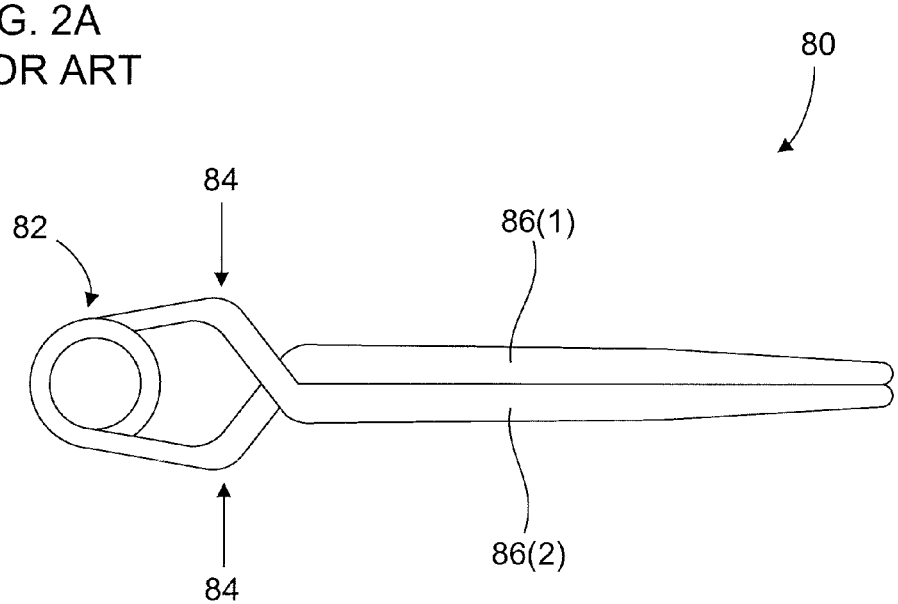
FIG. 2A is a top view of a prior art aneurysm clip.
Figure 2B:
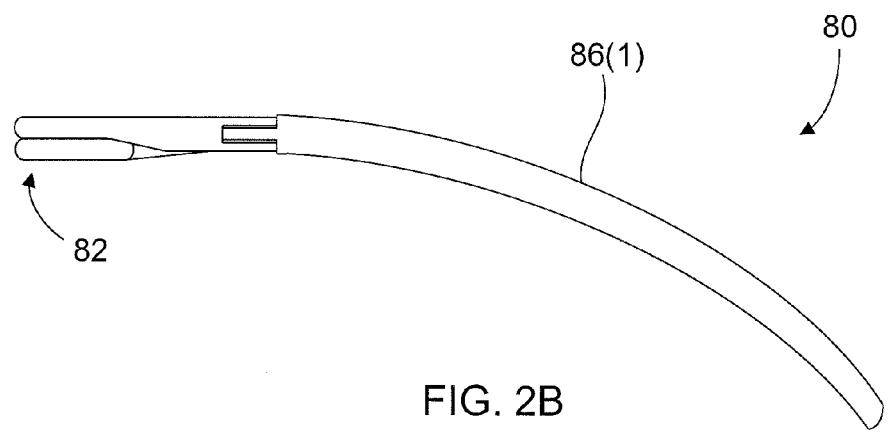
FIG. 2B is a side view of the prior art aneurysm clip of FIG. 2A.
Figure 14A:
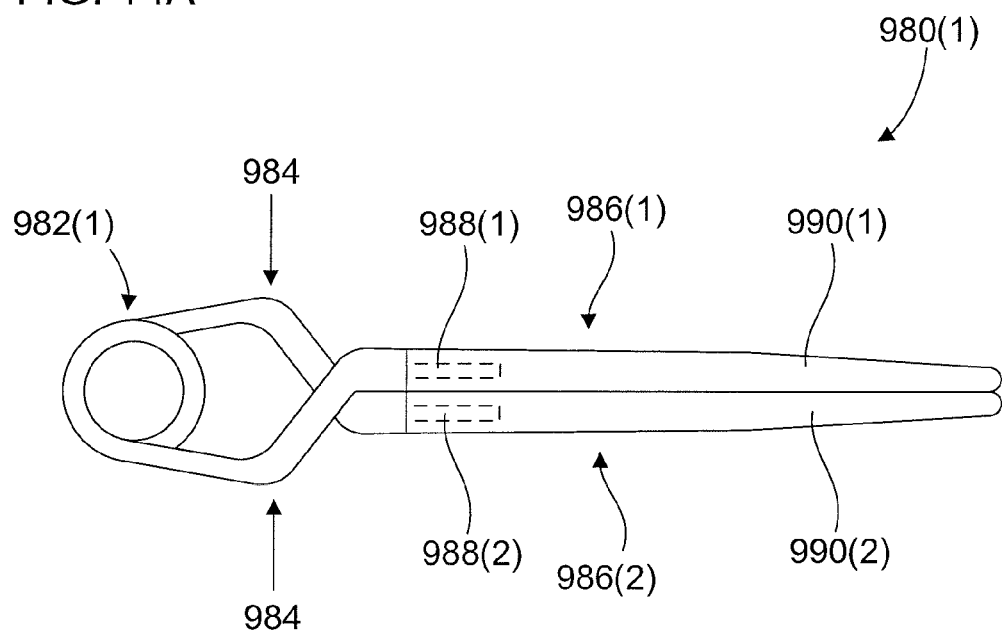
FIG. 14A shows an aneurysm clip.
Figure 14B:
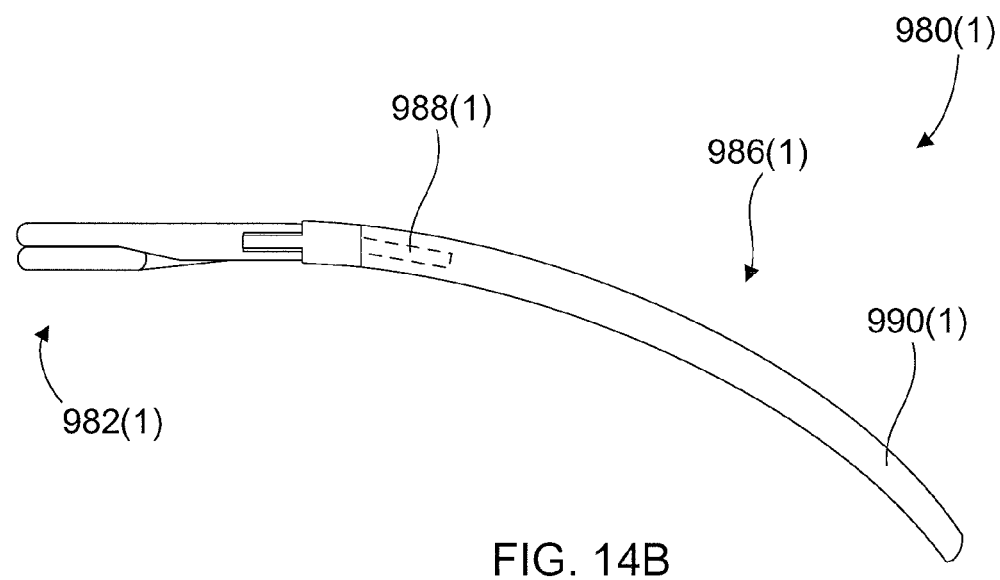
FIG. 14B shows a side view of the aneurysm clip of FIG. 14A.

FIG. 14A shows an aneurysm clip 980(1). Clip 980 has a spring 982(1) that biases jaws 986(1) and 986(2) into a closed position. A practitioner applying clip 980(1) uses an applicator tool (not shown) to squeeze clip 980(1) at points 984, forcing jaws 986(1) and 986(2) apart so that they may be positioned about a base of an aneurysm. The applicator tool may be the same tool used to apply prior art aneurysm clip 80, FIG. 2A and FIG. 2B. In clip 980(1), jaws 986(1) and 986(2) include stubs 988(1) and 988(2) and non-metallic blades 990(1) and 990(2), respectively. Non-metallic blades 990(1) and 990(2) may be made of, for example, polymethylmethacrylate, poly(etheretherketone), or carbon fiber. Non-metallic blades 990(1) and 990(2) do not introduce "flare" in angiographic images in the way that an equivalent metal element does (as demonstrated in FIG. 16A through FIG. 16E). Spring 982(1) and stubs 988(1) and 988(2) may be made of titanium, for example. Elements 990(1) and 990(2) mount over stubs 988(1) and 988(2); each such element 990 may bond to a corresponding stub 988 with an adhesive (e.g., epoxy glue) or may be press-fitted over stub 988. FIG. 14B shows a side view of clip 980(1); relative to the view shown in FIG. 14A, clip 980(1) is rolled towards the viewer so that jaw 986(1) is in front of, and blocks view of, jaw 986(2).

Use of non-metallic material for elements of an aneurysm clip may enable fabrication of complex contours and/or surface textures that may not be easily fabricated in metallic elements. Such contours may (a) decrease deflection of an aneurysm clip's jaws (e.g., jaws 986(1)-986(10), see also FIG. 15A-FIG. 15D) as compared to jaws of aneurysm clips that are made entirely of metal, and (b) allow fabrication of curves and angles suitable for clipping aneurysms of unusual shapes and/or locations. It is appreciated that non-metallic material may also be used for other parts of an aneurysm clip; for example, a spring or an entire aneurysm clip may be made from non-metallic material.

Figure 15A:
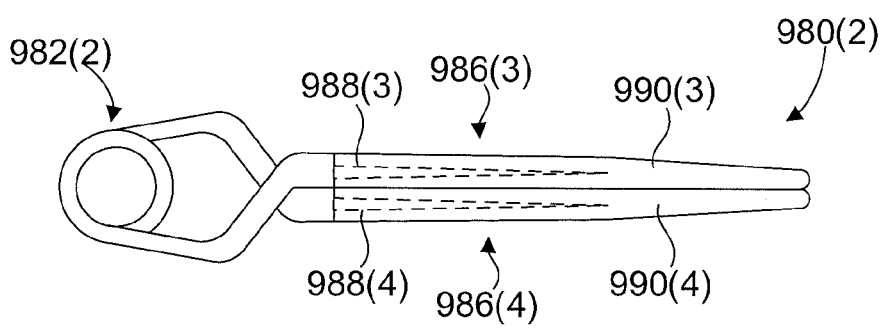
FIG. 15A through FIG. 15D show aneurysm clips.
Figure 15B:
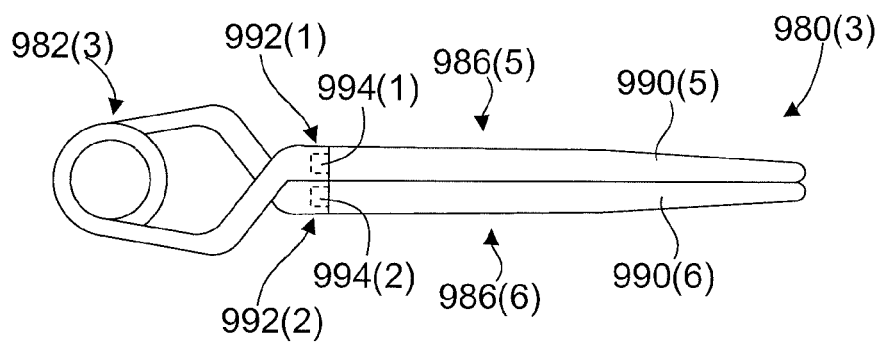
Figure 15C:
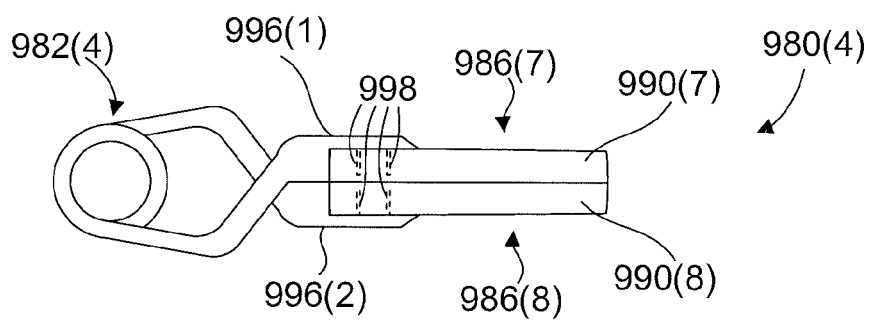

FIG. 15A through 15C show aneurysm clips 980(2) through 980(4). FIG. 15A shows aneurysm clip 980(2) that has spring 982(2) which biases jaws 986(3) and 986(4) into a closed position. In clip 980(2), jaws 986(3) and 986(4) include stubs 988(3) and 988(4) and non-metallic blades 990(3) and 990(4), respectively. Stubs 988(3) and 988(4) are longer than stubs 988(1) and 988(2) shown in FIG. 14A and FIG. 14B, but are narrower than jaws of aneurysm clips that do not use non-metallic blades 990(3) and 990(4), such that "flare" in angiographic images of clip 980(2) is accordingly reduced. FIG. 15B shows aneurysm clip 980(3) that has spring 982(3) which biases jaws 986(5) and 986(6) into a closed position. In clip 980(3), non-metallic blades 990(5) and 990(6) attach to spring 982(3) via non-metallic stubs 994(1) and 994(2) that are attached to cup fittings 992(1) and 992(2) with adhesive or by press-fitting. FIG. 15C shows aneurysm clip 980(4) that has spring 982(4) that biases jaws 986(7) and 986(8) into a closed position. In clip 980(4), non-metallic blades 990(7) and 990(8) attach to spring 982(4) via metal clamping elements 996(1) and 996(2) and pins 998 that extend partially through non-metallic blades 990(7) and 990(8).

Figure 15D:
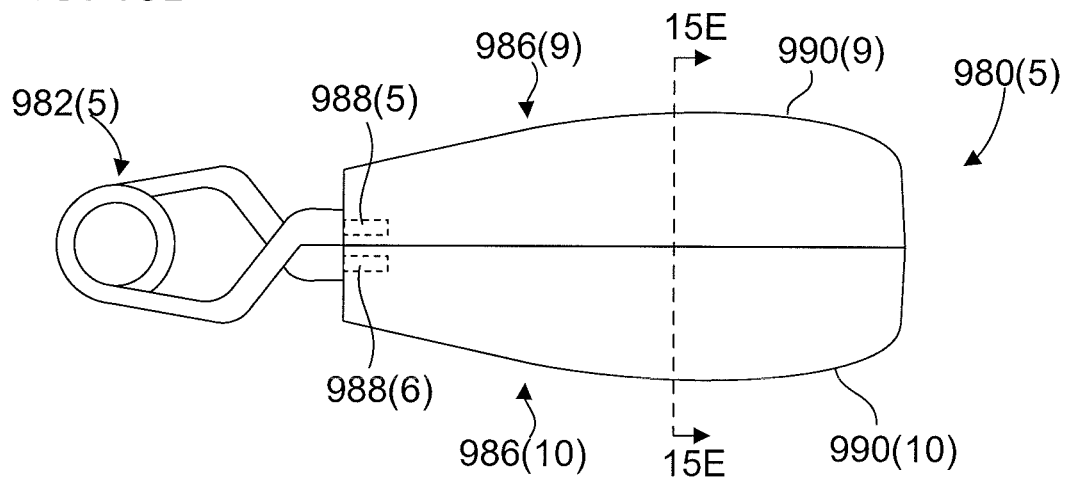
Figure 15E:
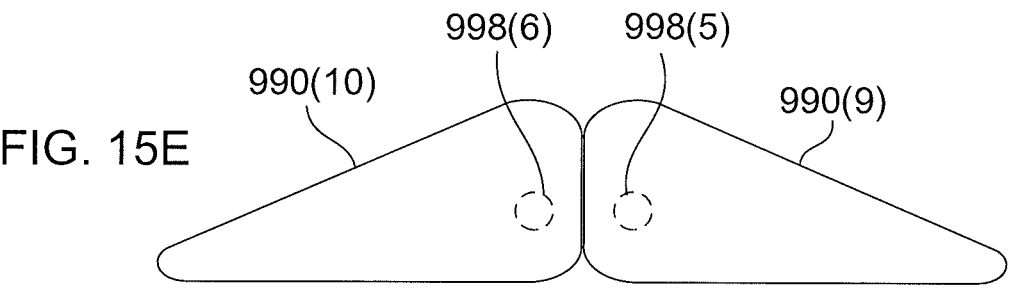
FIG. 15E and FIG. 15F are cross-sections of non-metallic blades of the aneurysm clip of FIG. 15D.
Figure 15F:
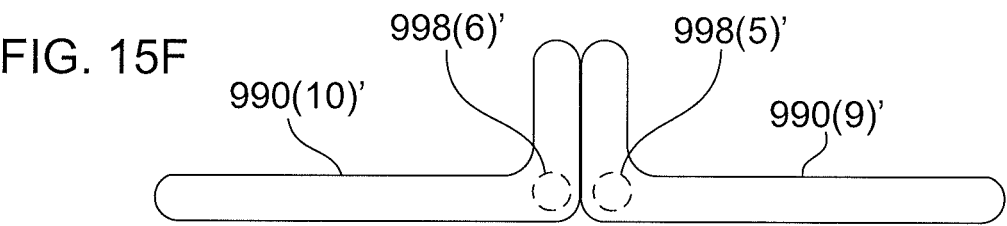

FIG. 15D shows an aneurysm clip 980(5) that has spring 982(5) that biases jaws 986(9) and 986(10) into a closed position. In clip 980(5), jaws 986(9) and 986(10) include stubs 988(5) and 988(6) and non-metallic blades 990(9) and 990(10), respectively. Non-metallic blades 990(9) and 990(10) are sized and shaped to reduce deflection, as compared to similarly sized metal elements, but produce less "flare" in angiographic images of clip 980(5) than is produced by a metallic aneurysm clip of similar dimensions. FIG. 15E is an enlarged cross-section of non-metallic blades 990(9) and 990(10) of aneurysm clip 980(5), taken along line 15E-15E of FIG. 15D. The use of non-metallic material in blades 990(9) and 990(10) facilitates fabrication of complex shapes such as those shown in FIG. 15E, which may provide additional support as compared with cylindrical blades. FIG. 15F is an enlarged cross-section of non-metallic blades 990(9)' and 990(10)' that can be used as blades 990(9) and 990(10) of clip 980(5), illustrating another advantageous shape that may be fabricated of non-metallic material.

Figure 16A:
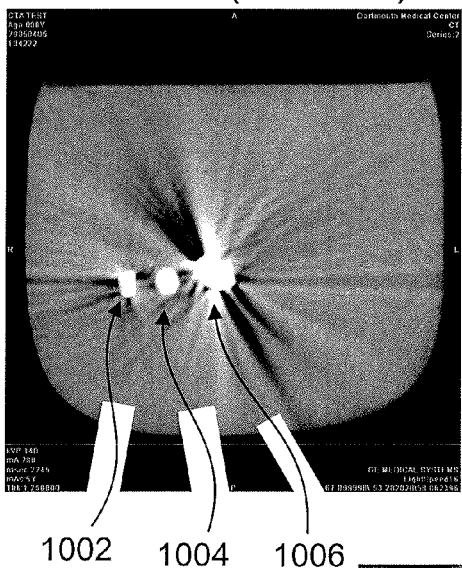
Figure 16B:
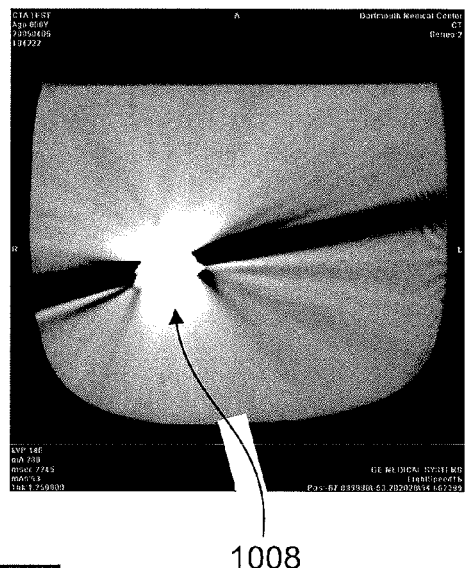
Figure 16C:
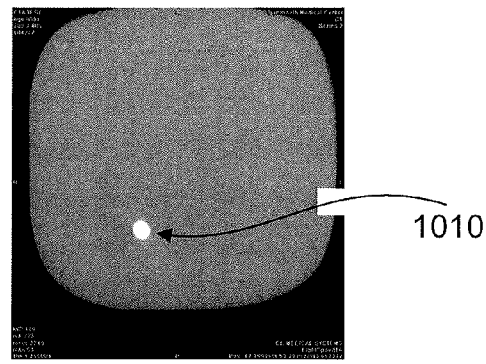
Figure 16D:
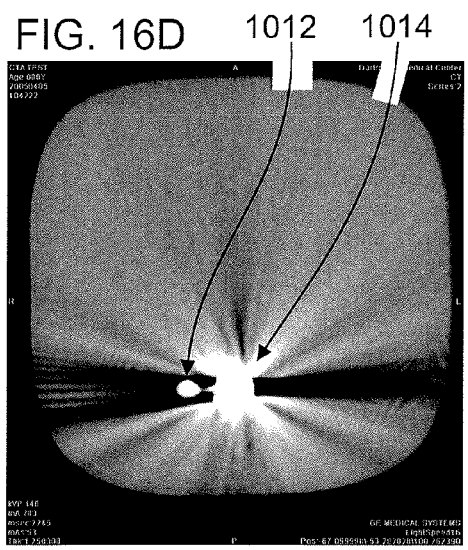
Figure 16D:
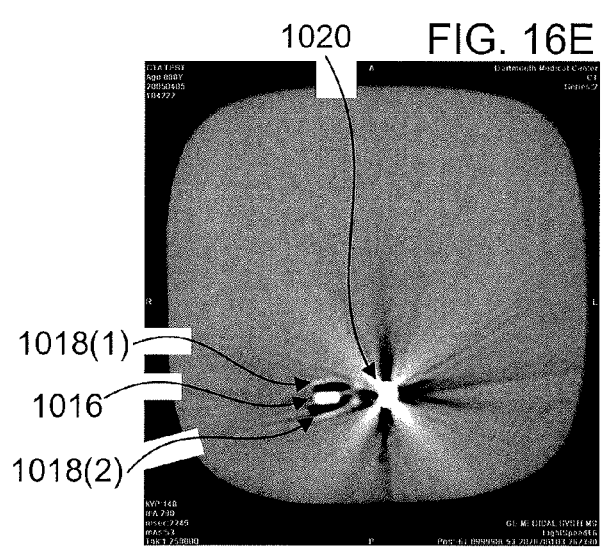

FIG. 16A through FIG. 16E demonstrate the reduced "flare" in angiographic images produced by aneurysm clips according to the present disclosure (e.g., any of clips 980(1) through 980(5)) as compared to prior art clips. A prior art aneurysm clip and an aneurysm clip with carbon fiber jaws were attached to a tube filled with angiographic contrast medium; the tube and the clips were suspended in a vessel of water for imaging. A stack of images was taken, each image corresponding to a different depth in the water; FIG. 16A through FIG. 16E are selected images from the stack of images. FIG. 16A and FIG. 16B show images with artifacts caused by the prior art aneurysm clip (e.g., like clip 80, FIG. 2). FIG. 16D and FIG. 16E show images with reduced artifacts due to the carbon fiber jaws. More particularly, in FIG. 16A, artifact 1002 is produced by tips of metallic jaws of the prior art clip, image 1004 is an image of the tube, and artifact 1006 is produced by a metallic spring. FIG. 16B is taken at a depth where jaws of the prior art clip clamp the tube; artifact 1008 produced by the prior art clip obscures the tube entirely. FIG. 16C shows an image 1010 of the tube alone (taken at a depth between the depths where the images of FIG. 16A and 16B and the images of FIG. 16C and FIG. 16D were taken). FIG. 16D shows an image 1012 of the tube and an artifact 1014 created by a metallic spring of the aneurysm clip, which corresponds to the maximum flare seen in any image at a depth corresponding to the aneurysm clip. FIG. 16E shows an image 1016 of the tube; artifacts 1018(1) and 1018(2) of carbon fiber jaws of the clip, and an artifact 1020 corresponding to the metallic spring of the clip. It is seen that FIG. 16D and FIG. 16E show reduction in the "flare" produced by metallic portions of a prior art clip, as compared to the images shown in FIG. 16A and FIG. 16B. In particular, image 1016 (of the tube, analogous to a blood vessel imaged during angiography) is clearly visible within FIG. 16E, but a corresponding image in FIG. 16B is obscured by "flare" produced by the prior art clip.

Figure 17:
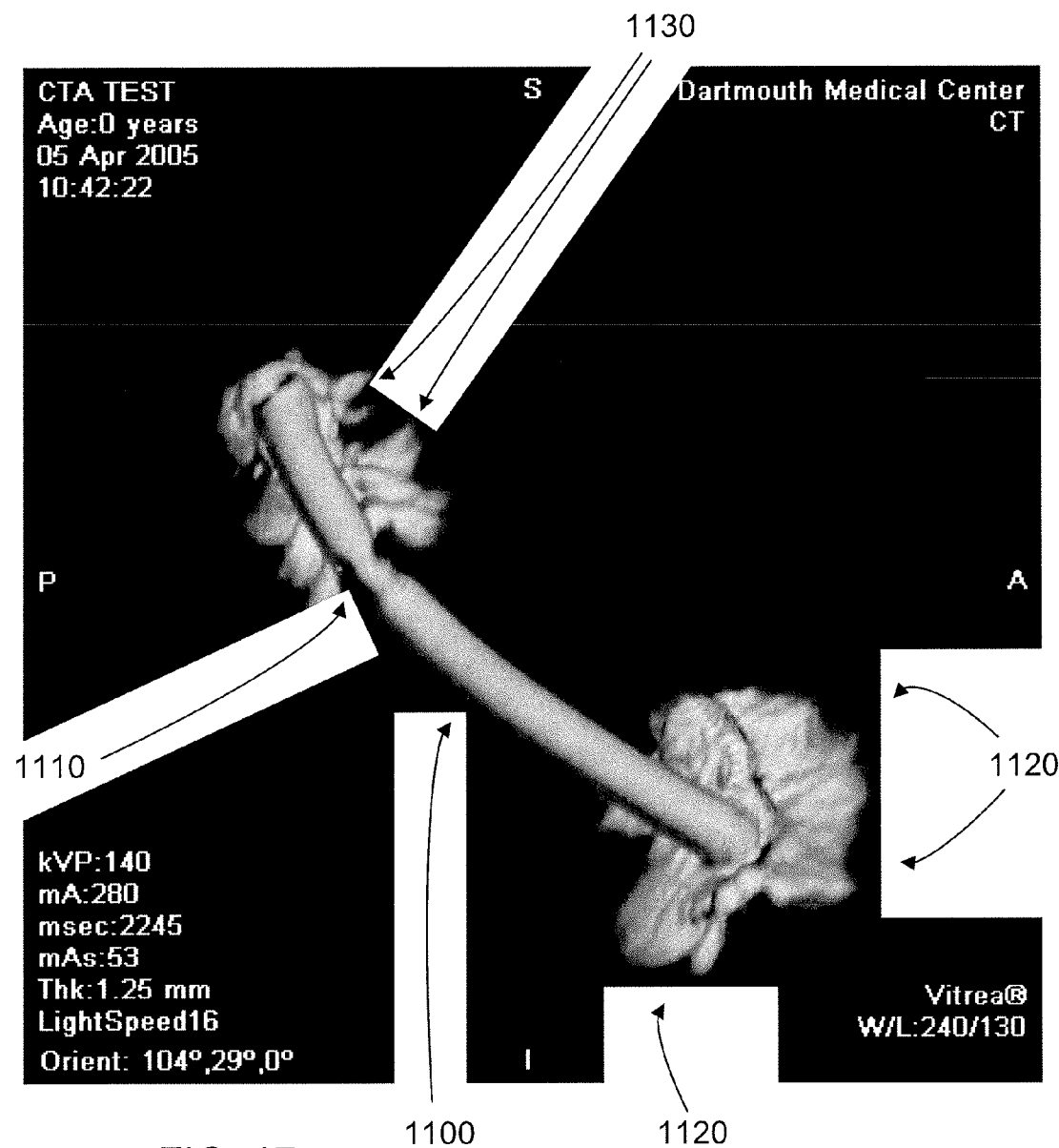
FIG. 17 shows a CT image reformatted from the stack of images from which FIG. 16A through FIG. 16E were selected.

FIG. 17 shows a CT image reformatted from the stack of images from which FIG. 16A through FIG. 16E were selected. A tube 1100 is filled with angiographic contrast medium. Arrow 1110 points to a location where tube 1100 is pinched by carbon fiber jaws of the aneurysm clip of the present disclosure (the carbon fiber jaws are not visible in the CT image). Arrow 1120 points to "flare" introduced by metal of the prior art aneurysm clip, and arrow 1130 points to reduced "flare" introduced by metal forming the spring of the aneurysm clip having carbon fiber jaws.

Figure 18A:
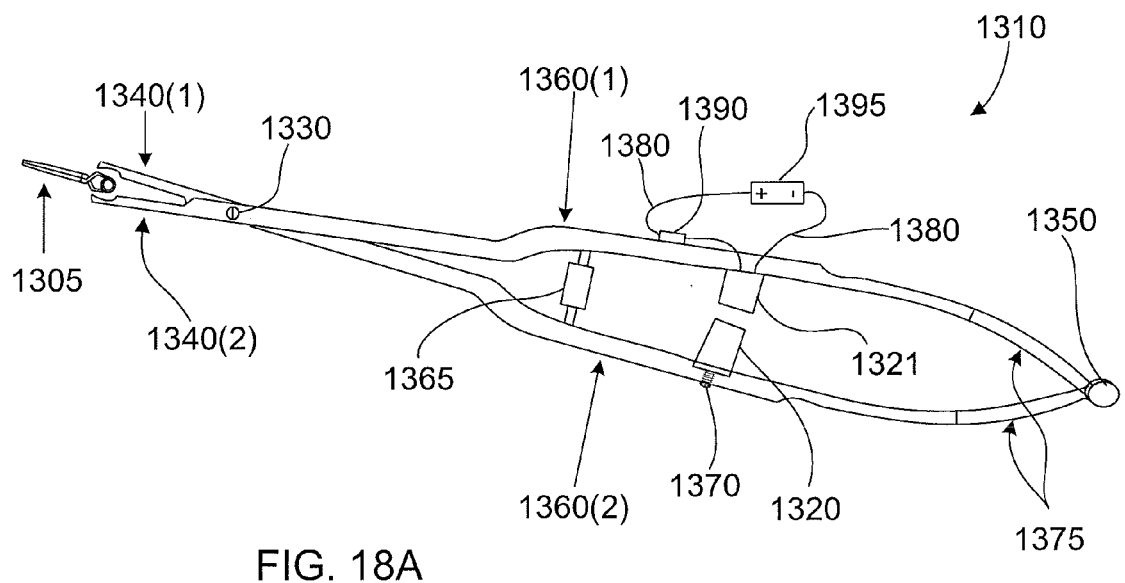
FIG. 18A and FIG. 18B show an aneurysm clip applicator in "open" and "closed" positions respectively.
Figure 18B:
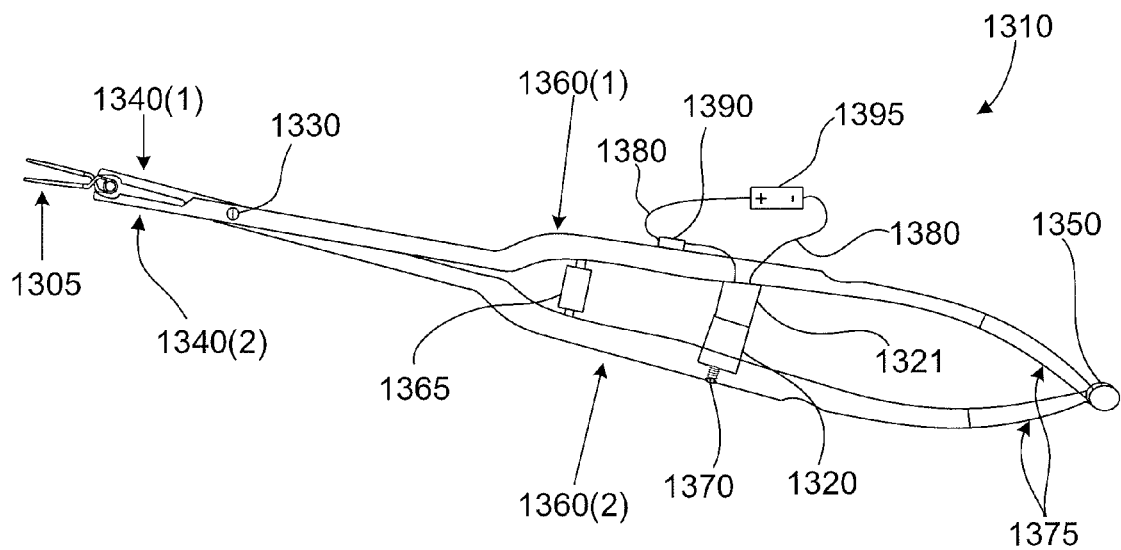

FIG. 18A and FIG. 18B show an aneurysm clip applicator 1310, according to an embodiment, in "open" and "closed" positions respectively. FIG. 18A and FIG. 18B may not be drawn to scale. Applicator 1310 includes handles 1360(1) and 1360(2) that a practitioner uses to operate jaws 1340(1) and 1340(2), which in turn operate an aneurysm clip 1305. An optional spring 1375 may be configured to bias handles 1360(1) and 1360(2) in an "open" position; FIG. 18A shows spring 1375 as a flat spring (e.g., formed from a strip of spring steel), but it is appreciated that another type of spring may be used as spring 1375. In FIG. 18A, handles 1360(1) and 1360(2) and spring 1375 are not compressed; applicator 1310 is thus in an "open" position, with jaws 1340(1) and 1340(2) in position to grasp clip 1305 (which is in a "closed" position). Applicator 1310 includes pivot points 1330 and 1350 that allow applicator 1310 to transition from the "open" position shown in FIG. 18A to the "closed" position shown in FIG. 18B.

Applicator 1310 also includes an electromagnet 1321, a power supply 1395 and a switch 1390. Wires 1380 connect electromagnet 1321, power supply 1395 and switch 1390. Electromagnet 1321 is deactivated and disengaged from a counter element 1320 while applicator 1310 is in the "open" position. An optional damping mechanism 1365 is also shown in FIG. 18A and is explained below.

In FIG. 18B, handles 1360(1) and 1360(2), and spring 1375 have been compressed by the practitioner, placing applicator 1310 into the "closed" position, such that jaws 1340(1) and 1340(2) force clip 1305 into the "open" position. When applicator 1310 is in the "closed" position, and the practitioner activates a switch 1390, power supply 1395 connects with electromagnet 1321, activating electromagnet 1321 so that it attracts counter element 1320, latching applicator 1310 in the "closed" position and clip 1305 in the "open" position.

Electromagnet 1321, counter element 1320, switch 1390, wires 1380 and power supply 1395 thus form an electromagnetic catch for applicator 1310. Latching applicator 1310 in the "closed" position allows the practitioner to manipulate applicator 1310 without the physical burden of maintaining pressure on handles 1360(1) and 1360(2). Switch 1390 may be advantageously placed on handle 1360(1) (or handle 1360(2)) where it is easily accessible (e.g., by a fingertip of the practitioner). Counter element 1320 may be, for example, a ferrous plate, or it may be a magnet of suitable polarity so as to be attracted to electromagnet 1321 when the electromagnet is magnetized.

When clip 1305 is in a final position for (e.g., in position for clipping an aneurysm), the practitioner may activate switch 1390 to disconnect power source 1395 from electromagnet 1321. Deactivation of electromagnet 1321 releases it from counter element 1320 so that applicator 1310 can return to the "open" position, closing clip 1305. Optional spring 1375 may assist in returning handles 1360(1) and 1360(2) to the "open" position. The release of handles 1360(1) and 1360(2) requires no additional motion by the practitioner, minimizing the risk of misplacing clip 1305. Optional damping mechanism 1365 may help eliminate any sudden jerk that may occur when electromagnet 1321 deactivates, and may control the speed at which handles 1360(1) and 1360(2) return to the "open" position, further minimizing the risk of misplacing clip 1305. It is contemplated that damping mechanism 1365 may be a small dashpot, a magnetic damping device or any other type of damping device known in the mechanical arts.

Position of counter element 1320 relative to handle 1360(2), according to one embodiment, may be adjustable by way of an optional screw 1370. The position of counter element 1320 relates to a distance between counter element 1320 and electromagnet 1321 when applicator 1310 is in the "open" state, which in turn relates to a distance that jaws 1340(1) and 1340(2) will open when applicator 1310 is in the "closed" state. Positioning counter element 1320 further away from handle 1360(2) reduces a distance that jaws 1340(1) and 1340(2) open. Use of screw 1370 to adjust this distance allows applicator 1310 to fit multiple clips 1305, and allows fine adjustments in the distance that clip 1305 opens.

It is appreciated that applicator 1310 may be custom fabricated to include electromagnet 1321, counter element 1320, switch 1390, power supply 1395 and, optionally, screw 1370, damping mechanism 1365 and/or spring 1375. Alternatively, electromagnet 1321, counter element 1320, switch 1390, power supply 1395 and, optionally, screw 1370, damping mechanism 1365 and/or spring 1375 may form a retrofit kit that can be installed on an existing applicator to add electromagnetic catch functionality.

Figure 19A:
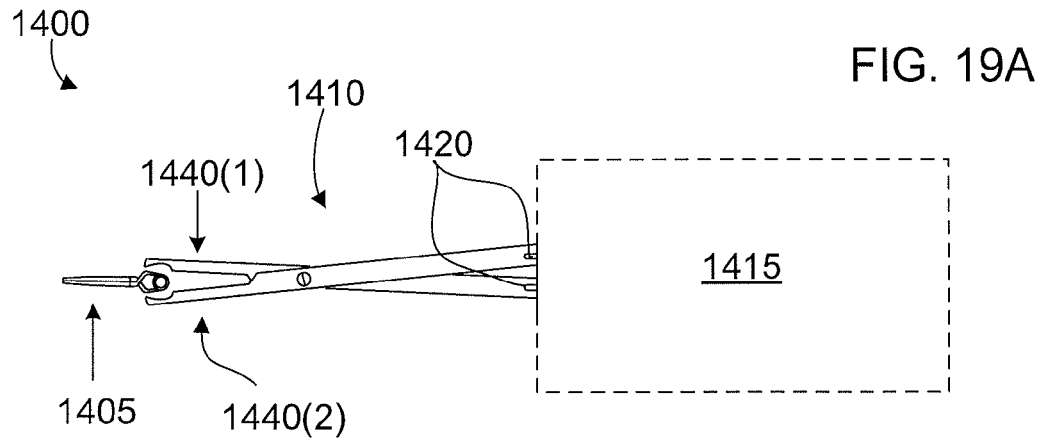
FIG. 19A shows an aneurysm clip applicator with a distal portion in an "open" position.

FIG. 19A shows an aneurysm clip applicator 1400, according to an embodiment, with a distal portion 1410 in an "open" position. Distal portion 1410 includes jaws 1440(1) and 1440(2) configured to engage clip 1405, and is manufactured of steel or titanium so that it is easily sterilized for reuse. An actuator portion 1415 connects to the distal portion 1410 by way of connectors 1420. Connectors 1420 may include male-female devices as shown, latches, or other hardware for locking jaws 1440(1) and 1440(2) to actuator portion 1415. Actuator portion 1415 may be sterilizable and reusable, or may be manufactured for single use and subsequent disposal.

Figure 19B:
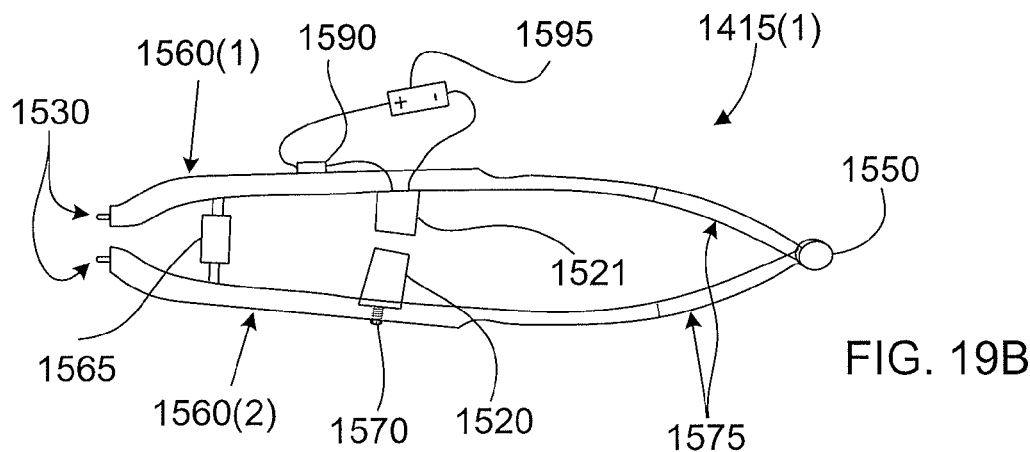
FIG. 19B shows an actuator portion that may be form part of the aneurysm clip applicator of FIG. 19A.

FIG. 19B shows an actuator portion 1415(1), according to an embodiment, that may be used as actuator portion 1415 of aneurysm clip applicator 1400. Actuator portion 1415(1) includes connector elements 1530 (male connector elements are shown), that secure portion 1415(1) to distal portion 1410 (see FIG. 19A). Actuator portion 1415(1) includes handles 1560(1) and 1560(2) that a practitioner compresses to operate jaws to open an aneurysm clip. Actuator portion 1415(1) also includes an optional spring 1575 and a damping mechanism 1565.

Once distal portion 1410 attaches to actuator portion 1415(1) to form applicator 1400, operation is much like operation of applicator 1310, FIG. 18A and FIG. 18B. Electromagnet 1521 and a counter element 1520 disengage while applicator 1400 is in the "open" position. The practitioner may activate a switch 1590 to connect a power supply 1595 with an electromagnet 1521, magnetizing electromagnet 1521 so that it attracts counter element 1520, latching applicator 1400 in the "closed" position with clip 1405 in an "open" position. The practitioner may then activate switch 1590 to disconnect power source 1595 and electromagnet 1521, releasing electromagnet 1521 from counter element 1520. Spring 1575 may then decompress, returning handles 1560(1) and 1560(2), and applicator 1400 to the "open" position so that clip 1405 closes. Optional damping device 1565 may control the speed at which applicator 1400 returns to the "open" position. Position of counter element 1520 relative to handle 1560(2), according to one embodiment, is adjustable by way of optional screw 1570. Actuator portion 1415(1) includes pivot point 1530, which allows applicator 1400 to transition between "open" and "closed" positions.

Figure 19C:
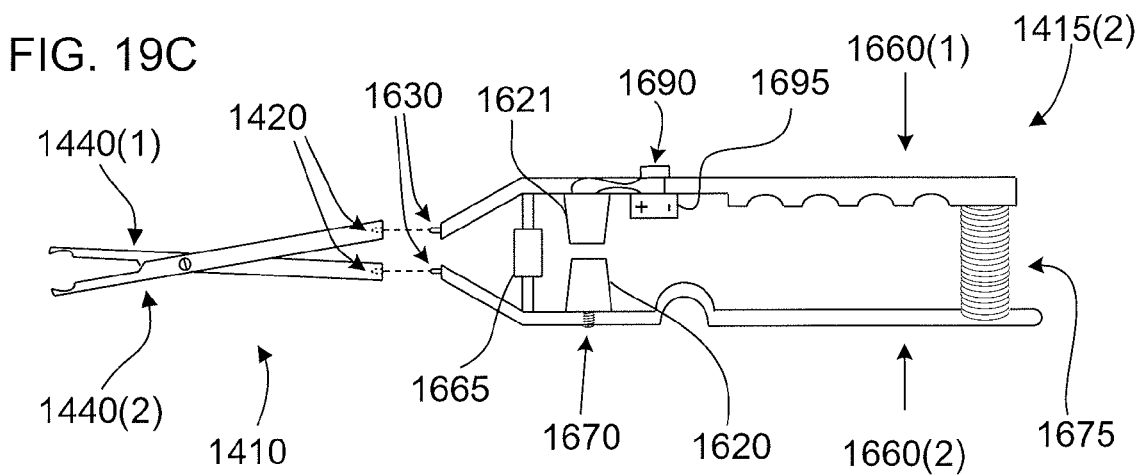
FIG. 19C is an exploded diagram illustrating how an actuator portion and the distal portion of FIG. 19A may cooperate to form an aneurysm clip applicator, according to an embodiment.

FIG. 19C is an exploded diagram illustrating how an actuator portion 1415(2) and distal portion 1410 may cooperate to form an aneurysm clip applicator 1400(1), according to an embodiment. Actuator portion 1415(2) includes connector elements 1630, (male connector elements are shown), that secure portion 1415(2) to distal portion 1410 (see FIG. 19A). Actuator portion 1415(2) includes handles 1660(1) and 1660(2) that a practitioner compresses to operate jaws to open an aneurysm clip. Actuator portion 1415(2) also includes an optional spring 1675 (shown as a coil spring) and a damping mechanism 1665. Once distal portion 1410 attaches to actuator portion 1415(2) to form applicator 1400, operation is much like operation of applicator 1310.

Figure 3A:
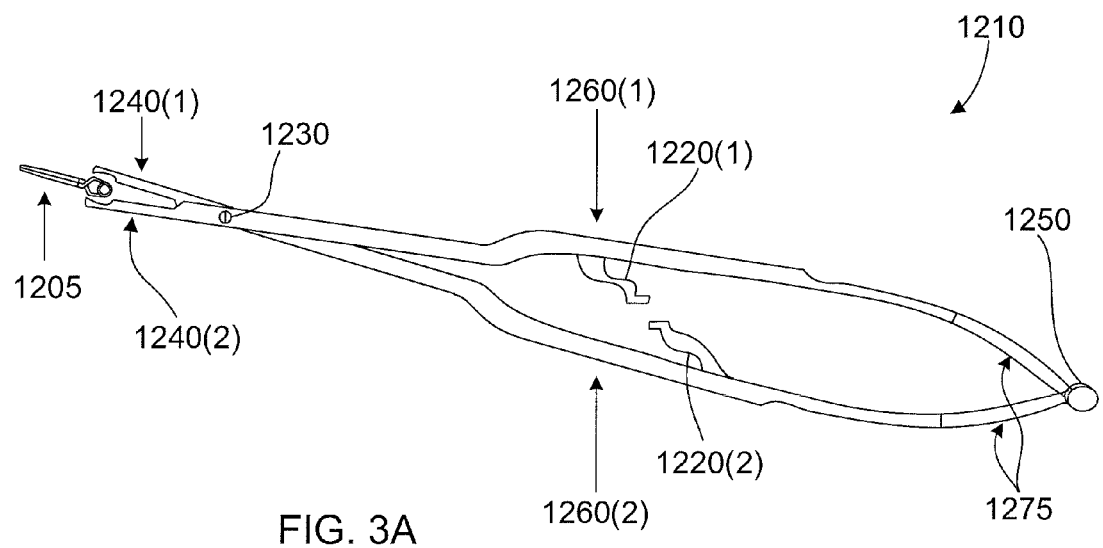
FIG. 3A shows the prior art aneurysm clip of FIG. 2A in an open position.
Figure 3B:
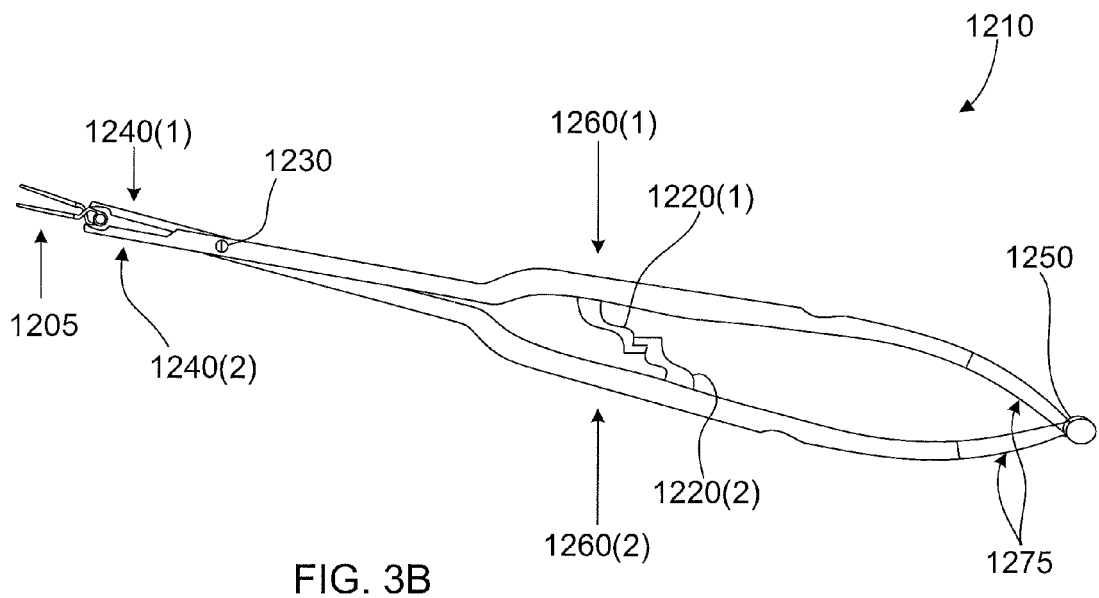
FIG. 3B shows the prior art aneurysm clip of FIG. 2A in a closed position.

Actuator portion 1415 may, for example, include plastic components and be considered disposable; alternatively, actuator portion 1415 may include metal (e.g., steel or titanium) components that can be sterilized and reused. Thus, for example, an applicator according to the present disclosure could be created (1) by retrofitting electromagnetic catch components to an existing applicator (such as the applicator shown in FIG. 3A and FIG. 3B), (2) by manufacture of a one-piece applicator, or (3) by manufacture of distal and Actuator portions as shown in FIG. 19A, FIG. 19B and FIG. 19C.

The changes described above, and others, may be made in the wire torque apparatus, wire insertion devices, aneurysm clips and aneurysm clip applicators described herein without departing from the scope hereof. For example, gripping features of torque devices or wire insertion devices may be protrusions (e.g., like gripping features 145 of FIG. 4A), facets (e.g., like the hexagonal faces shown in FIG. 5A, FIG. 5B, FIG. 5C, FIG. 6A and FIG. 6B), finger indentations (e.g., like gripping features 655 of FIG. 10A, FIG. 10B, FIG. 10C and FIG. 10D), loops (e.g., like gripping elements 755 of FIG. 11), grooves, pits, or raised features. A handle with a crossbar, like handles 640(1), 640(2) and crossbar 630 may be used with wire insertion devices like device 810. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A wire torque apparatus, comprising
an outer block forming (a) a first lengthwise slot at a first end and extending within the outer block, and (b) a tapered cavity at a second end and extending within the outer block, the tapered cavity including:
   (c) a tapered, internally threaded cavity portion proximate the second end, and
   (d) a tapered, nonthreaded cavity portion connecting the first lengthwise slot and the internally threaded portion; and
an inner block forming (a) a second lengthwise slot (b) a plurality of tapered externally threaded elements, and (c) a tongue proximate the externally threaded elements, extending outward from a tip of the inner block and past the externally threaded elements;
wherein the first and second lengthwise slots are configured to accommodate passage of a length of wire therethrough when the slots are aligned, such that the apparatus can clamp the wire without threading an end of the wire through the apparatus, and wherein the threaded elements are configured to screw the inner block at least partially into the tapered cavity of the outer block to engage the wire; and
wherein, upon initial engagement of the externally threaded elements with the internally threaded cavity portion, the tongue blocks the wire from entering the first lengthwise slot, and upon further engagement, the tongue advances past the nonthreaded cavity portion and deforms against the wire to bias the wire against an inner surface of the outer block, to hold the wire in place within the tapered cavity.

2. The wire torque apparatus of claim 1, the outer and inner blocks being hexagonal in cross-section.

3. The wire torque apparatus of claim 1, the outer and inner blocks rotatable between an open position for accommodating the length of wire and a closed position for holding the wire in place, the tongue blocking the wire from the slot in the closed position.

4. An improved wire torque apparatus of a type that is configured to clamp a length of wire therein, the improvement wherein structure of the apparatus forms:
inner and outer elements configured for engaging with one another such that the inner element screws at least partially into the outer element; and
a lengthwise slot configured to accommodate passage of the wire such that the apparatus can clamp onto the wire without threading an end of the wire through the apparatus;
wherein the inner element includes a tongue extending from a tip of the inner element, and
wherein the outer element forms a tapered cavity for accepting the inner element, the tapered cavity having an opening, a tapered, internally threaded portion proximate the opening and a tapered, nonthreaded portion proximate the internally threaded portion;
wherein upon initial engagement of the inner element with the threaded cavity portion, the tongue blocks the wire from entering the slot, and upon further engagement, the tongue advances within the nonthreaded portion and deforms against the wire to bias the wire against an inner surface of the outer element, to hold the wire in place within a tapered cavity of the outer element.

5. The wire torque apparatus of claim 4, the lengthwise slot comprising a first slot in the inner element and a second slot in the outer element, the first and second slots configured to accommodate passage of the wire when aligned, wherein the second slot in the outer element connects with the nonthreaded portion of the tapered cavity.

6. The wire torque apparatus of claim 5, wherein alignment of the first and second slots facilitates insertion of the wire into the apparatus from a direction oblique to a direction of the lengthwise slot.

7. The wire torque apparatus of claim 4, the lengthwise slot formed when first and second lengthwise sub-slots of the apparatus are aligned, and wherein:
the inner element comprises a handle at an end of the inner element opposite the tongue;
the outer element comprises a cap forming the tapered cavity and the second lengthwise sub-slot, the cap configured for engaging the handle; and
the first and second sub-slots are configured to accommodate passage of a length of wire therethrough when the sub-slots are aligned to form the lengthwise slot, and wherein the tongue is configured to bias the wire against an inner surface of the tapered cavity when the cap engages the handle.

* * * * *